(12) United States Patent
Nagata et al.

(10) Patent No.: US 9,042,972 B2
(45) Date of Patent: May 26, 2015

(54) PAIN JUDGING DEVICE TO JUDGE PAIN BASED ON A FREQUENCY COMPONENT OF A PEAK-RELEVANT VALUE

(75) Inventors: Shinya Nagata, Osaka (JP); Ryuji Nagai, Osaka (JP); Keiko Yamamoto, Kanagawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 410 days.

(21) Appl. No.: 13/000,925

(22) PCT Filed: Jun. 23, 2009

(86) PCT No.: PCT/JP2009/002866
§ 371 (c)(1),
(2), (4) Date: Dec. 22, 2010

(87) PCT Pub. No.: WO2009/157185
PCT Pub. Date: Dec. 30, 2009

(65) Prior Publication Data
US 2011/0112420 A1 May 12, 2011

(30) Foreign Application Priority Data
Jun. 24, 2008 (JP) .................................. 2008-164466

(51) Int. Cl.
*A61B 5/0456* (2006.01)
*A61B 5/04* (2006.01)
(Continued)

(52) U.S. Cl.
CPC ........... *A61B 5/04014* (2013.01); *A61B 5/0452* (2013.01); *A61B 5/4824* (2013.01); *A61B 5/7203* (2013.01)

(58) Field of Classification Search
CPC . A61B 5/04014; A61B 5/0452; A61B 5/4824
USPC ......................................... 600/509, 517, 516
See application file for complete search history.

(56) References Cited

U.S. PATENT DOCUMENTS 6,258,042 B1  7/2001 Factor et al.
6,315,736 B1 * 11/2001 Tsutsumi et al. ............. 600/500
(Continued)

FOREIGN PATENT DOCUMENTS

JP      9-285512 A    11/1997
JP   2000-342690 A    12/2000
(Continued)

OTHER PUBLICATIONS

International Search Report prepared by the Japanese Patent Office dated Jul. 28, 2009, for International Application No. PCT/JP2009/002866.
(Continued)

*Primary Examiner* — Christopher D Koharski
*Assistant Examiner* — Michael Carey
(74) *Attorney, Agent, or Firm* — Jason H. Vick; Sheridan Ross, PC

(57) ABSTRACT

A peak-relevant value device acquires a peak-relevant value (for example, the peak value of an R wave (R peak value)) every cycle from an electrocardiogram acquired. The frequencies of the peak-relevant value acquired as time-series data and the magnitudes for the respective frequencies are analyzed. A peak-relevant value LF calculating device calculates an LF component (peak-relevant value LF component) from the frequency component of the peak-relevant value. An interval acquiring device acquires the interval between characteristic points of the electrocardiographic complex from the electrocardiogram acquired and the frequencies of the feature point interval acquired as time-series data to acquire the magnitudes of the respective frequency component are analyzed. An interval HF calculating device calculates the HF component from the frequency components of the feature point interval acquired and pain is judged on the basis of the variations of the peak-relevant value LF components and the interval HF components.

10 Claims, 21 Drawing Sheets

(51) Int. Cl.
*A61B 5/0452* (2006.01)
*A61B 5/00* (2006.01)

(56) References Cited

U.S. PATENT DOCUMENTS

| 6,339,720 | B1 * | 1/2002 | Anzellini et al. | 600/517 |
|---|---|---|---|---|
| 2004/0015091 | A1 * | 1/2004 | Greenwald et al. | 600/513 |
| 2005/0033189 | A1 * | 2/2005 | McCraty et al. | 600/509 |
| 2008/0132801 | A1 * | 6/2008 | Logier et al. | 600/523 |
| 2008/0249430 | A1 * | 10/2008 | John et al. | 600/544 |

FOREIGN PATENT DOCUMENTS

| JP | 2005-521505 A | 7/2005 |
|---|---|---|
| JP | 2006-130121 A | 5/2006 |
| JP | 2008-513073 A | 5/2008 |
| WO | WO 2003/084396 | 4/2003 |

OTHER PUBLICATIONS

Written Opinion (including English translation) for International (PCT) Application No. PCT/JP2009/002866, mailed Jul. 28, 2009, 9 pages.

International Preliminary Report on Patentability (including English translation) for International (PCT) Application No. PCT/JP2009/002866, issued Feb. 8, 2011, 11 pages.

Official Action (including translation) for Chinese Patent Application No. 200980123632.4, issued Dec. 23, 2011.

Official Action (including translation) for Chinese Patent Application No. 200980123632.4, issued Aug. 28, 2012.

* cited by examiner

FIG.6A

| ABSOLUTE TIME | LAPSE | P(t) | P | P' | Q | R | S | STj | T(t) | T | T' | RR | P (Pb-Pe) | PR | VAT | QRS | QT | QTc | HR (BPM) | Mark | Status |
|---|---|---|---|---|---|---|---|---|---|---|---|---|---|---|---|---|---|---|---|---|---|
| 09:24:01 | 7.580 | -0.042 | -0.042 | 0.000 | 0.299 | 2.417 | -0.257 | 0.909 | 1.270 | 1.270 | 0.000 | 679 | 85 | 166 | 39 | 107 | 384 | 466 | 88 | 0 | 256 |
| 09:24:02 | 8.243 | 0.398 | 0.398 | 0.000 | 0.218 | 1.760 | -0.388 | 0.503 | 0.890 | 0.890 | 0.000 | 663 | 82 | 193 | 40 | 114 | 314 | 386 | 90 | 0 | 256 |
| 09:24:02 | 8.899 | 0.375 | 0.375 | 0.000 | -0.565 | 1.378 | -1.079 | -0.357 | 0.303 | 0.303 | 0.000 | 656 | 117 | 142 | 75 | 119 | 361 | 446 | 91 | 0 | 16 |
| 09:24:03 | 9.536 | 0.076 | 0.076 | 0.000 | 0.012 | 2.267 | -1.026 | 0.038 | 1.229 | 1.229 | 0.000 | 637 | 37 | 90 | 38 | 85 | 361 | 452 | 94 | 0 | 0 |
| 09:24:04 | 10.191 | 0.228 | 0.228 | 0.000 | -0.312 | 1.766 | -1.347 | -0.332 | 0.668 | 0.668 | 0.000 | 655 | 44 | 223 | 43 | 89 | 348 | 430 | 92 | 0 | 0 |
| 09:24:04 | 10.822 | 0.081 | 0.081 | 0.000 | -0.096 | 1.931 | -0.964 | -0.058 | 0.691 | 0.691 | 0.000 | 631 | 110 | 172 | 35 | 86 | 335 | 422 | 95 | 0 | 0 |
| 09:24:05 | 11.448 | 0.093 | 0.093 | 0.000 | -0.067 | 2.010 | -0.941 | -0.064 | 0.667 | 0.667 | 0.000 | 626 | 93 | 168 | 33 | 84 | 334 | 422 | 96 | 0 | 0 |
| 09:24:06 | 12.065 | 0.101 | 0.101 | 0.000 | -0.230 | 1.908 | -0.968 | -0.174 | 0.551 | 0.551 | 0.000 | 617 | 105 | 152 | 52 | 101 | 328 | 418 | 97 | 0 | 0 |
| 09:24:06 | 12.670 | 0.153 | 0.153 | 0.000 | -0.082 | 2.176 | -0.924 | -0.055 | 0.838 | 0.838 | 0.000 | 605 | 98 | 244 | 35 | 79 | 316 | 406 | 99 | 0 | 0 |
| 09:24:07 | 13.262 | 0.145 | 0.145 | 0.000 | -0.365 | 1.940 | -1.223 | -0.242 | 0.843 | 0.843 | 0.000 | 592 | 33 | 163 | 68 | 112 | 355 | 461 | 101 | 0 | 0 |
| 09:24:07 | 13.854 | 0.136 | 0.136 | 0.000 | -0.315 | 1.878 | -1.412 | -0.317 | 0.997 | 0.997 | 0.000 | 592 | 91 | 162 | 52 | 94 | 356 | 463 | 101 | 0 | 256 |
| 09:24:08 | 14.456 | 0.185 | 0.185 | 0.000 | -0.116 | 2.024 | -1.089 | 0.038 | 1.059 | 1.059 | 0.000 | 602 | 114 | 151 | 55 | 104 | 339 | 437 | 100 | 0 | 0 |
| 09:24:09 | 15.077 | 0.008 | 0.008 | 0.000 | -0.155 | 2.120 | -1.001 | -0.032 | 0.803 | 0.803 | 0.000 | 621 | 44 | 61 | 43 | 94 | 334 | 424 | 97 | 0 | 8 |
| 09:24:09 | 15.739 | 0.199 | 0.199 | 0.000 | -0.338 | 1.799 | -1.049 | -0.151 | 0.862 | 0.862 | 0.000 | 662 | 72 | 221 | 66 | 112 | 372 | 457 | 91 | 0 | 32 |
| 09:24:10 | 16.436 | 0.100 | 0.100 | 0.000 | -0.096 | 2.111 | -0.933 | -0.053 | 0.786 | 0.786 | 0.000 | 697 | 37 | 119 | 40 | 89 | 340 | 407 | 86 | 0 | 0 |
| 09:24:11 | 17.133 | 0.107 | 0.107 | 0.000 | -0.030 | 2.099 | -0.942 | -0.032 | 0.846 | 0.846 | 0.000 | 697 | 105 | 157 | 44 | 92 | 345 | 413 | 86 | 0 | 0 |
| 09:24:11 | 17.835 | 0.092 | 0.092 | 0.000 | -0.068 | 2.025 | -0.937 | -0.051 | 0.805 | 0.805 | 0.000 | 702 | 117 | 176 | 41 | 89 | 341 | 407 | 85 | 0 | 0 |
| 09:24:12 | 18.542 | 0.084 | 0.084 | 0.000 | -0.091 | 1.973 | -0.873 | -0.069 | 0.797 | 0.797 | 0.000 | 707 | 113 | 163 | 48 | 94 | 359 | 427 | 85 | 0 | 0 |
| 09:24:13 | 19.265 | 0.123 | 0.123 | 0.000 | -0.013 | 2.162 | -0.850 | 0.051 | 0.884 | 0.884 | 0.000 | 723 | 114 | 185 | 29 | 81 | 348 | 409 | 83 | 0 | 0 |
| 09:24:13 | 19.985 | 0.116 | 0.116 | 0.000 | -0.072 | 2.106 | -0.938 | -0.051 | 0.859 | 0.859 | 0.000 | 720 | 120 | 177 | 41 | 89 | 341 | 402 | 83 | 0 | 0 |
| 09:24:14 | 20.705 | 0.101 | 0.101 | 0.000 | -0.048 | 2.152 | -0.901 | 0.012 | 0.918 | 0.918 | 0.000 | 720 | 100 | 168 | 33 | 85 | 347 | 409 | 83 | 0 | 0 |
| 09:24:15 | 21.485 | 0.114 | 0.114 | 0.000 | 0.016 | 2.131 | -0.788 | 0.077 | 0.882 | 0.882 | 0.000 | 780 | 100 | 169 | 31 | 82 | 328 | 371 | 77 | 0 | 0 |
| 09:24:16 | 22.311 | 0.104 | 0.104 | 0.000 | -0.037 | 2.043 | -0.827 | -0.006 | 0.863 | 0.863 | 0.000 | 826 | 126 | 192 | 33 | 82 | 333 | 366 | 73 | 0 | 0 |
| 09:24:17 | 23.173 | 0.185 | 0.185 | 0.000 | -0.055 | 2.074 | -0.916 | -0.050 | 0.791 | 0.791 | 0.000 | 862 | 29 | 92 | 35 | 81 | 359 | 387 | 70 | 0 | 0 |
| 09:24:18 | 24.004 | 0.052 | 0.052 | 0.000 | -0.184 | 2.070 | -1.189 | -0.024 | 0.780 | 0.780 | 0.000 | 831 | 18 | 68 | 78 | 134 | 397 | 436 | 72 | 0 | 0 |
| 09:24:18 | 24.749 | 0.334 | 0.334 | 0.000 | 0.253 | 2.505 | -0.414 | 0.690 | 1.593 | 1.593 | 0.000 | 745 | 30 | 53 | 81 | 134 | 387 | 448 | 81 | 0 | 2 |
| 09:24:19 | 25.499 | 0.208 | 0.208 | 0.000 | -0.289 | 1.910 | -1.243 | -0.226 | 0.865 | 0.865 | 0.000 | 750 | 82 | 254 | 36 | 83 | 339 | 391 | 80 | 0 | 2 |

FIG.6B

| ABSOLUTE TIME | RELATIVE TIME (SECOND) | P(') | P | P' | Q | R | S | STj | T(') | T | T' | RR | P (Pb-Pe) | PR | VAT | QRS | QT | QTc | HR (BPM) | P(') | P |
|---|---|---|---|---|---|---|---|---|---|---|---|---|---|---|---|---|---|---|---|---|---|
| 09:24:29 | 35 | 0.196 | 0.196 | 0.000 | 0.111 | 2.040 | -0.773 | 0.119 | 1.046 | 1.046 | 0.000 | 816.0 | 132.0 | 205.0 | 32.5 | 81.5 | 343.0 | 382.6 | 73.5 | 0.149 | 0.149 |
| 09:24:34 | 40 | 0.207 | 0.207 | 0.000 | 0.018 | 2.126 | -0.790 | 0.132 | 1.107 | 1.107 | 0.000 | 935.0 | 106.0 | 165.0 | 47.0 | 97.7 | 367.3 | 377.0 | 64.2 | 0.147 | 0.147 |
| 09:24:39 | 45 | 0.139 | 0.139 | 0.000 | -0.014 | 2.197 | -0.835 | 0.027 | 1.006 | 1.006 | 0.000 | 918.2 | 107.0 | 179.2 | 37.8 | 88.8 | 348.3 | 363.6 | 65.3 | 0.145 | 0.145 |
| 09:24:44 | 50 | 0.127 | 0.127 | 0.000 | -0.021 | 2.189 | -0.877 | 0.012 | 1.033 | 1.033 | 0.000 | 859.7 | 109.3 | 176.5 | 38.3 | 88.8 | 353.8 | 382.2 | 69.8 | 0.142 | 0.142 |
| 09:24:49 | 55 | 0.127 | 0.127 | 0.000 | -0.041 | 2.172 | -0.887 | -0.014 | 0.997 | 0.997 | 0.000 | 912.2 | 105.8 | 176.8 | 39.8 | 89.8 | 355.8 | 372.9 | 65.8 | 0.140 | 0.140 |
| 09:24:54 | 60 | 0.119 | 0.119 | 0.000 | -0.027 | 2.227 | -0.874 | 0.000 | 1.025 | 1.025 | 0.000 | 927.6 | 120.0 | 183.6 | 42.6 | 93.2 | 359.8 | 373.6 | 64.7 | 0.138 | 0.138 |
| 09:24:59 | 65 | 0.136 | 0.136 | 0.000 | -0.016 | 2.293 | -0.863 | 0.004 | 1.073 | 1.073 | 0.000 | 925.5 | 123.2 | 185.3 | 42.0 | 92.2 | 360.7 | 374.9 | 64.8 | 0.137 | 0.137 |
| 09:25:04 | 70 | 0.127 | 0.127 | 0.000 | -0.022 | 2.295 | -0.853 | 0.017 | 1.100 | 1.100 | 0.000 | 956.4 | 122.8 | 183.2 | 44.0 | 94.8 | 363.4 | 371.7 | 62.7 | 0.135 | 0.135 |
| 09:25:09 | 75 | 0.129 | 0.129 | 0.000 | -0.019 | 2.343 | -0.884 | 0.007 | 1.104 | 1.104 | 0.000 | 975.2 | 123.2 | 188.2 | 38.4 | 88.8 | 360.2 | 364.8 | 61.5 | 0.134 | 0.134 |
| 09:25:14 | 80 | 0.134 | 0.134 | 0.000 | -0.012 | 2.333 | -0.886 | -0.002 | 1.121 | 1.121 | 0.000 | 985.4 | 121.8 | 191.0 | 37.8 | 87.4 | 358.8 | 361.5 | 60.9 | 0.133 | 0.133 |
| 09:25:19 | 85 | 0.131 | 0.131 | 0.000 | -0.026 | 2.316 | -0.874 | -0.004 | 1.120 | 1.120 | 0.000 | 970.8 | 113.2 | 189.4 | 39.6 | 89.6 | 366.6 | 372.1 | 61.8 | 0.133 | 0.133 |
| 09:25:24 | 90 | | | | | 2.281 | | | | | | 972.3 | | | | | | | | | 0.132 |
| 09:25:29 | 95 | 0.133 | 0.133 | 0.000 | -0.016 | 2.146 | -0.862 | 0.020 | 1.131 | 1.131 | 0.000 | 970.8 | 118.2 | 183.0 | 43.0 | 92.4 | 372.4 | 379.7 | 61.8 | 0.130 | 0.130 |
| 09:25:34 | 100 | 0.131 | 0.131 | 0.000 | 0.006 | 2.149 | -0.875 | 0.025 | 1.115 | 1.115 | 0.000 | 957.4 | 106.5 | 170.8 | 41.0 | 91.5 | 378.5 | 389.6 | 62.7 | 0.128 | 0.128 |
| 09:25:39 | 105 | | | | | 2.082 | | | | | | 960.4 | | | | | | | | 0.127 | 0.127 |
| 09:25:44 | 110 | 0.132 | 0.132 | 0.000 | -0.022 | 2.111 | -0.881 | 0.010 | 1.066 | 1.066 | 0.000 | 861.8 | 114.8 | 175.3 | 36.2 | 87.6 | 366.4 | 384.8 | 69.6 | 0.127 | 0.127 |
| 09:25:49 | 115 | 0.123 | 0.123 | 0.000 | -0.023 | 2.133 | -0.821 | -0.001 | 1.052 | 1.052 | 0.000 | 938.2 | 117.0 | 184.4 | 37.2 | 87.8 | 372.4 | 384.5 | 64.0 | 0.130 | 0.130 |
| 09:25:54 | 120 | 0.109 | 0.109 | 0.000 | -0.041 | 2.146 | -0.864 | -0.009 | 1.083 | 1.083 | 0.000 | 819.2 | 110.6 | 179.6 | 36.6 | 86.6 | 368.4 | 407.6 | 73.2 | 0.133 | 0.133 |
| 09:25:59 | 125 | 0.126 | 0.126 | 0.000 | -0.028 | 2.179 | -0.833 | -0.016 | 1.081 | 1.081 | 0.000 | 958.4 | 102.4 | 181.6 | 36.8 | 85.8 | 371.8 | 380.4 | 62.6 | 0.139 | 0.139 |
| 09:26:04 | 130 | 0.119 | 0.119 | 0.000 | -0.012 | 2.147 | -0.791 | 0.002 | 1.075 | 1.075 | 0.000 | 983.0 | 122.6 | 184.8 | 37.8 | 86.8 | 371.4 | 374.3 | 61.0 | 0.147 | 0.147 |
| 09:26:09 | 135 | 0.133 | 0.133 | 0.000 | -0.071 | 2.104 | -0.860 | -0.045 | 1.027 | 1.027 | 0.000 | 983.8 | 104.3 | 181.7 | 39.3 | 88.3 | 380.3 | 380.7 | 61.0 | 0.152 | 0.152 |
| 09:26:14 | 140 | 0.185 | 0.185 | 0.000 | -0.010 | 2.260 | -0.838 | 0.081 | 1.178 | 1.178 | 0.000 | 952.2 | 96.3 | 170.3 | 44.0 | 98.8 | 381.0 | 390.3 | 63.0 | 0.155 | 0.155 |
| 09:26:19 | 145 | 0.150 | 0.150 | 0.000 | -0.029 | 2.136 | -0.823 | 0.015 | 1.097 | 1.097 | 0.000 | 1007.4 | 79.3 | 173.3 | 44.5 | 94.5 | 381.0 | 381.1 | 59.6 | 0.156 | 0.156 |
| 09:26:24 | 150 | 0.172 | 0.172 | 0.000 | -0.014 | 2.202 | -0.804 | 0.030 | 1.162 | 1.162 | 0.000 | 974.4 | 101.6 | 179.8 | 44.8 | 92.6 | 385.8 | 390.9 | 61.6 | 0.156 | 0.156 |
| 09:26:29 | 155 | 0.195 | 0.195 | 0.000 | 0.005 | 2.209 | -0.742 | 0.073 | 1.192 | 1.192 | 0.000 | 1019.5 | 85.3 | 182.5 | 44.8 | 94.8 | 388.5 | 384.8 | 58.9 | 0.155 | 0.155 |
| 09:26:34 | 160 | 0.163 | 0.163 | 0.000 | 0.008 | 2.274 | -0.801 | 0.049 | 1.163 | 1.163 | 0.000 | 961.2 | 113.0 | 185.8 | 41.2 | 93.0 | 384.4 | 392.0 | 62.4 | 0.155 | 0.155 |
| 09:26:39 | 165 | 0.137 | 0.137 | 0.000 | -0.019 | 2.228 | -0.813 | -0.004 | 1.102 | 1.102 | 0.000 | 976.4 | 125.6 | 191.2 | 36.2 | 86.0 | 378.6 | 383.2 | 61.5 | 0.157 | 0.157 |

RR INTERVAL

| ABSO-LUTE TIME | RELATIVE TIME (SECOND) | RELATIVE TIME (MINUTE) | LF Amplitude | HF Amplitude | LF Peak Frq (Hz) | HF Peak Frq (Hz) | LF Amplitude (HIGH-FREQUENCY CUTOFF) | HF Amplitude (HIGH-FREQUENCY CUTOFF) |
|---|---|---|---|---|---|---|---|---|
| 09:25:29 | 95 | 1.583 | 47.318 | 0.000 | 0.120 | 0.000 | 49.216 | 6.592 |
| 09:25:34 | 100 | 1.667 | 41.371 | 11.743 | 0.111 | 0.146 | 51.760 | 8.023 |
| 09:25:39 | 105 | 1.750 | 35.397 | 15.968 | 0.083 | 0.174 | 51.225 | 9.170 |
| 09:25:44 | 110 | 1.833 | 44.510 | 8.339 | 0.102 | 0.135 | 48.363 | 10.153 |
| 09:25:49 | 115 | 1.917 | 65.378 | 13.022 | 0.096 | 0.274 | 45.236 | 10.770 |
| 09:25:54 | 120 | 2.000 | 84.055 | 10.717 | 0.101 | 0.116 | 42.630 | 11.009 |
| 09:25:59 | 125 | 2.083 | 70.093 | 15.593 | 0.078 | 0.187 | 40.332 | 11.005 |
| 09:26:04 | 130 | 2.167 | 15.621 | 9.068 | 0.086 | 0.230 | 38.269 | 10.820 |
| 09:26:09 | 135 | 2.250 | 2.751 | 13.325 | 0.074 | 0.278 | 35.505 | 10.254 |
| 09:26:14 | 140 | 2.333 | 26.095 | 8.972 | 0.078 | 0.260 | 31.657 | 9.571 |
| 09:26:19 | 145 | 2.417 | 38.244 | 7.042 | 0.102 | 0.126 | 27.583 | 8.837 |
| 09:26:24 | 150 | 2.500 | 36.178 | 9.718 | 0.112 | 0.246 | 23.358 | 8.324 |
| 09:26:29 | 155 | 2.583 | 33.796 | 6.963 | 0.110 | 0.143 | 19.135 | 8.083 |
| 09:26:34 | 160 | 2.667 | 22.118 | 3.729 | 0.097 | 0.145 | 15.614 | 8.223 |
| 09:26:39 | 165 | 2.750 | 1.513 | 4.768 | 0.115 | 0.181 | 14.290 | 8.976 |
| 09:26:44 | 170 | 2.833 | 6.499 | 5.783 | 0.107 | 0.156 | 15.137 | 9.642 |
| 09:26:49 | 175 | 2.917 | 6.921 | 7.616 | 0.110 | 0.162 | 16.516 | 10.106 |
| 09:26:54 | 180 | 3.000 | 0.795 | 10.522 | 0.110 | 0.209 | 17.009 | 10.631 |
| 09:26:59 | 185 | 3.083 | 9.701 | 11.940 | 0.122 | 0.256 | 16.594 | 11.035 |
| 09:27:04 | 190 | 3.167 | 24.570 | 20.239 | 0.116 | 0.211 | 15.757 | 11.002 |
| 09:27:09 | 195 | 3.250 | 49.157 | 11.064 | 0.071 | 0.165 | 14.999 | 10.918 |
| 09:27:14 | 200 | 3.333 | 35.246 | 10.039 | 0.071 | 0.138 | 14.276 | 10.966 |
| 09:27:19 | 205 | 3.417 | 9.277 | 12.738 | 0.064 | 0.182 | 13.285 | 10.785 |
| 09:27:24 | 210 | 3.500 | 4.552 | 12.888 | 0.123 | 0.177 | 12.625 | 10.602 |

FIG.10

R WAVE PEAK VALUE

| ABSOLUTE TIME | RELATIVE TIME (SECOND) | RELATIVE TIME (MINUTE) | LF Amplitude | HF Amplitude | LF Peak Frq (Hz) | HF Peak Frq (Hz) | LF Amplitude (HIGH-FREQUENCY CUTOFF) | HF Amplitude (HIGH-FREQUENCY CUTOFF) |
|---|---|---|---|---|---|---|---|---|
| 09:25:29 | 95  | 1.583 | 0.033 | 0.024 | 0.068 | 0.247 | 0.033 | 0.014 |
| 09:25:34 | 100 | 1.667 | 0.019 | 0.016 | 0.069 | 0.237 | 0.031 | 0.017 |
| 09:25:39 | 105 | 1.750 | 0.026 | 0.010 | 0.072 | 0.284 | 0.029 | 0.019 |
| 09:25:44 | 110 | 1.833 | 0.001 | 0.014 | 0.059 | 0.202 | 0.031 | 0.023 |
| 09:25:49 | 115 | 1.917 | 0.015 | 0.027 | 0.125 | 0.153 | 0.037 | 0.025 |
| 09:25:54 | 120 | 2.000 | 0.051 | 0.029 | 0.137 | 0.114 | 0.043 | 0.027 |
| 09:25:59 | 125 | 2.083 | 0.021 | 0.032 | 0.093 | 0.235 | 0.047 | 0.029 |
| 09:26:04 | 130 | 2.167 | 0.018 | 0.029 | 0.062 | 0.191 | 0.050 | 0.031 |
| 09:26:09 | 135 | 2.250 | 0.082 | 0.042 | 0.081 | 0.246 | 0.053 | 0.031 |
| 09:26:14 | 140 | 2.333 | 0.104 | 0.031 | 0.083 | 0.280 | 0.053 | 0.033 |
| 09:26:19 | 145 | 2.417 | 0.095 | 0.029 | 0.076 | 0.282 | 0.052 | 0.035 |
| 09:26:24 | 150 | 2.500 | 0.031 | 0.042 | 0.074 | 0.247 | 0.050 | 0.037 |
| 09:26:29 | 155 | 2.583 | 0.047 | 0.030 | 0.128 | 0.280 | 0.046 | 0.038 |
| 09:26:34 | 160 | 2.667 | 0.057 | 0.017 | 0.121 | 0.223 | 0.041 | 0.039 |
| 09:26:39 | 165 | 2.750 | 0.029 | 0.042 | 0.140 | 0.177 | 0.040 | 0.038 |
| 09:26:44 | 170 | 2.833 | 0.046 | 0.062 | 0.140 | 0.176 | 0.043 | 0.036 |
| 09:26:49 | 175 | 2.917 | 0.012 | 0.042 | 0.114 | 0.182 | 0.048 | 0.035 |
| 09:26:54 | 180 | 3.000 | 0.012 | 0.033 | 0.093 | 0.231 | 0.054 | 0.034 |
| 09:26:59 | 185 | 3.083 | 0.019 | 0.035 | 0.112 | 0.264 | 0.058 | 0.034 |
| 09:27:04 | 190 | 3.167 | 0.043 | 0.023 | 0.097 | 0.222 | 0.061 | 0.033 |
| 09:27:09 | 195 | 3.250 | 0.120 | 0.011 | 0.107 | 0.070 | 0.065 | 0.033 |
| 09:27:14 | 200 | 3.333 | 0.103 | 0.035 | 0.084 | 0.176 | 0.065 | 0.033 |
| 09:27:19 | 205 | 3.417 | 0.083 | 0.038 | 0.094 | 0.188 | 0.061 | 0.034 |
| 09:27:24 | 210 | 3.500 | 0.058 | 0.035 | 0.089 | 0.188 | 0.057 | 0.035 |

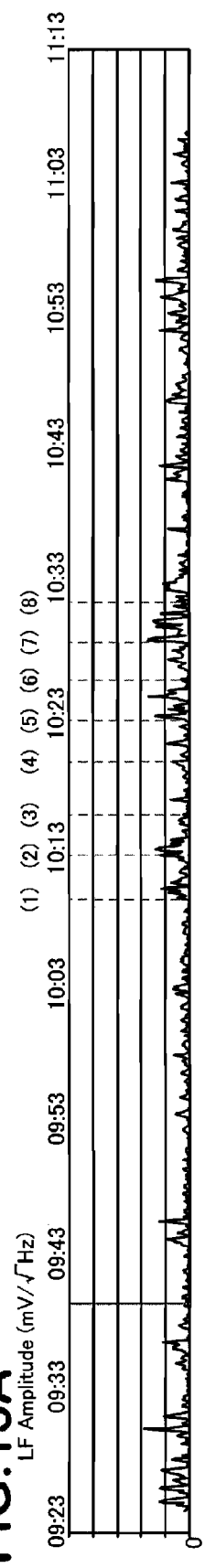
FIG.15A
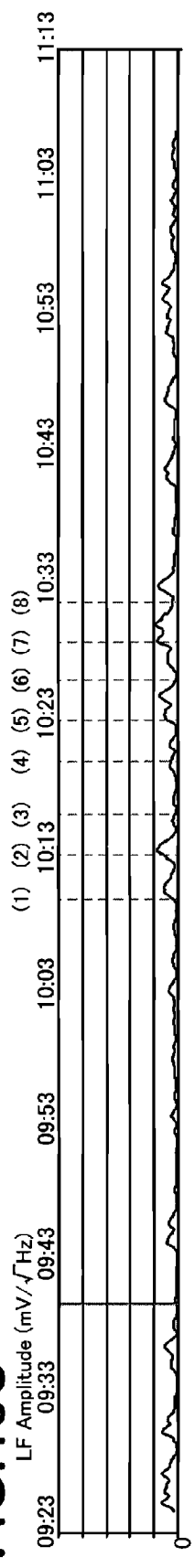
FIG.15B
FIG.15C
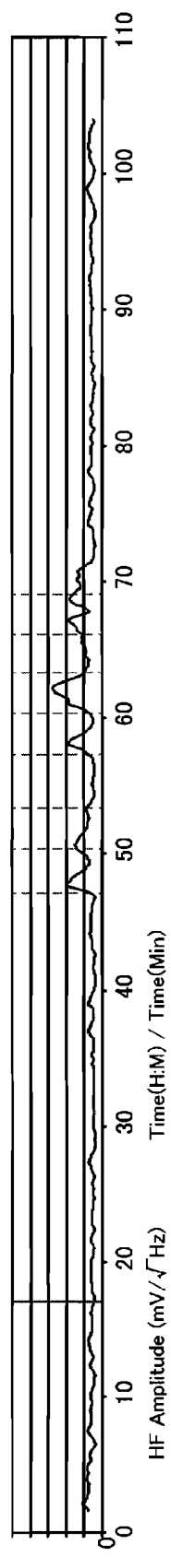
FIG.15D

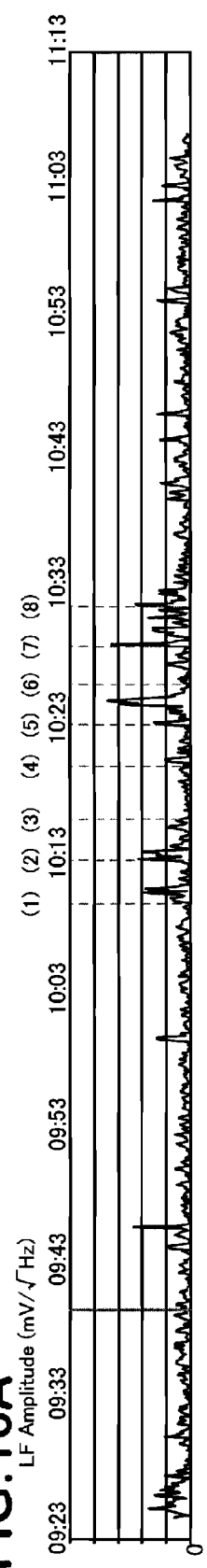
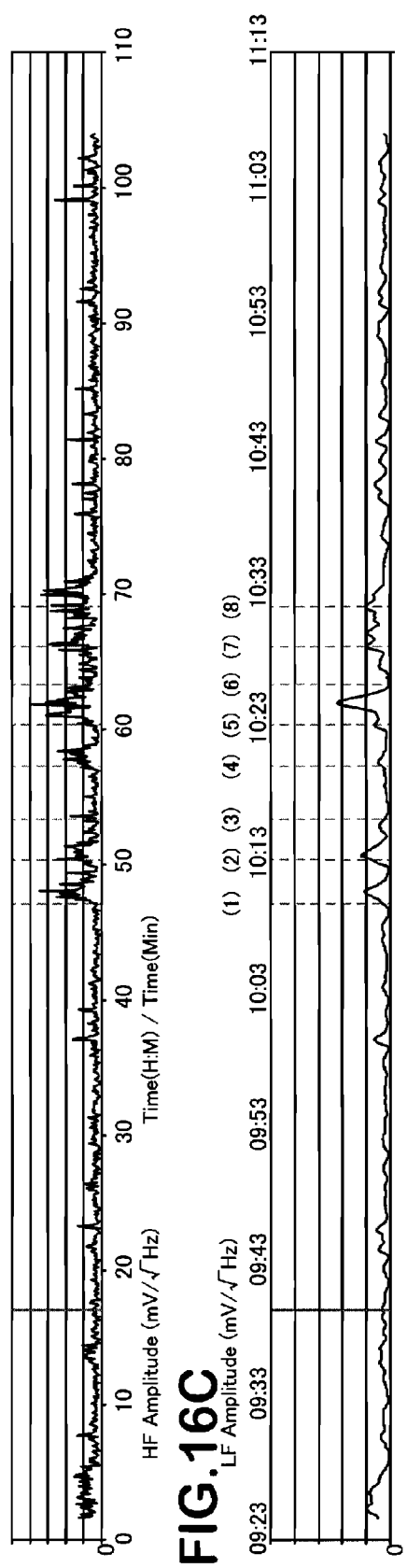
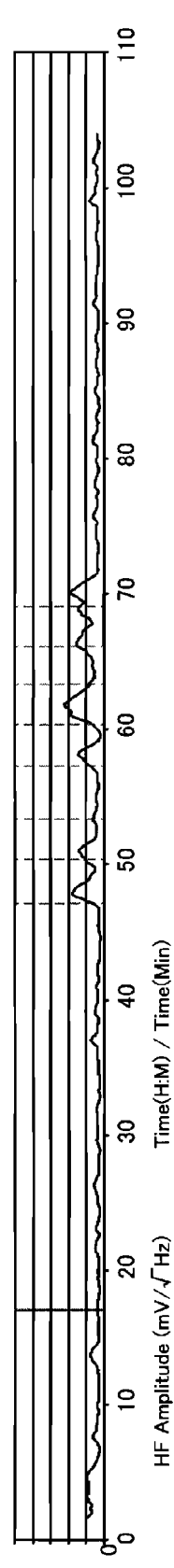

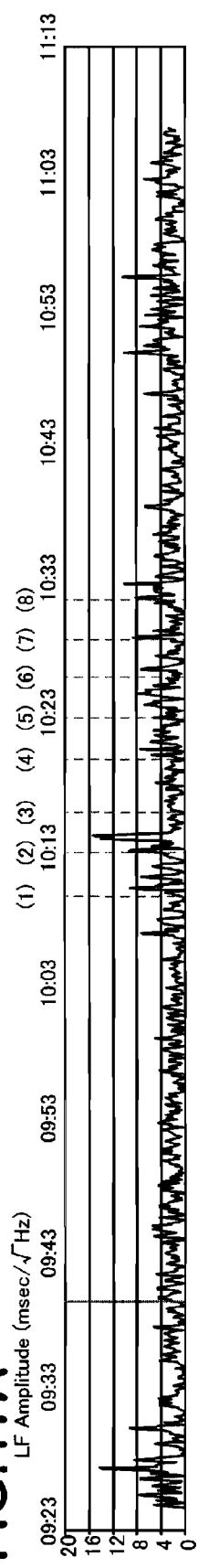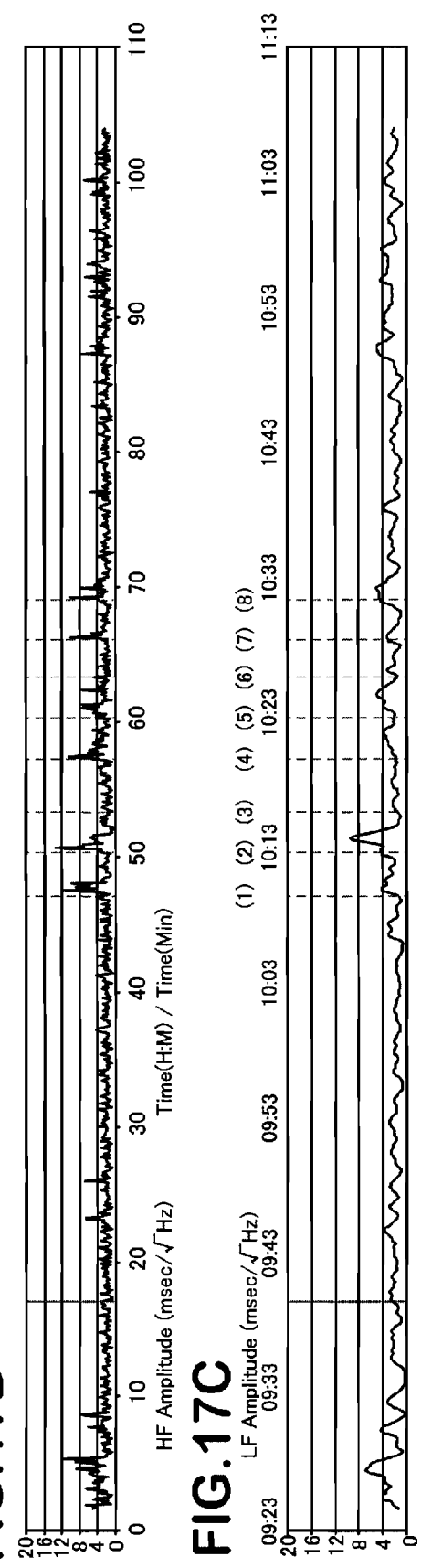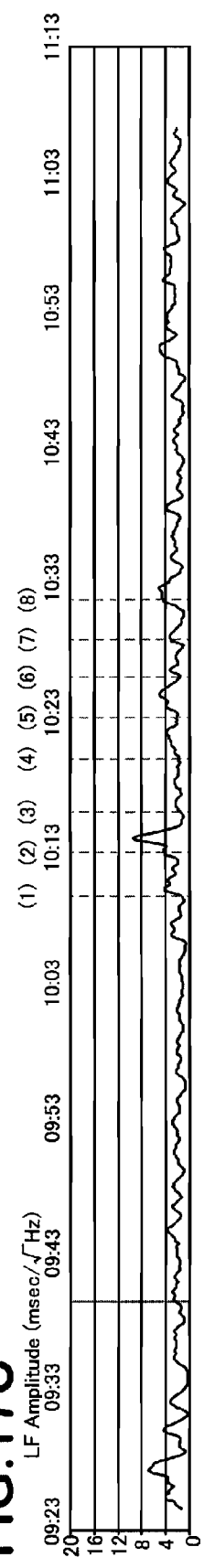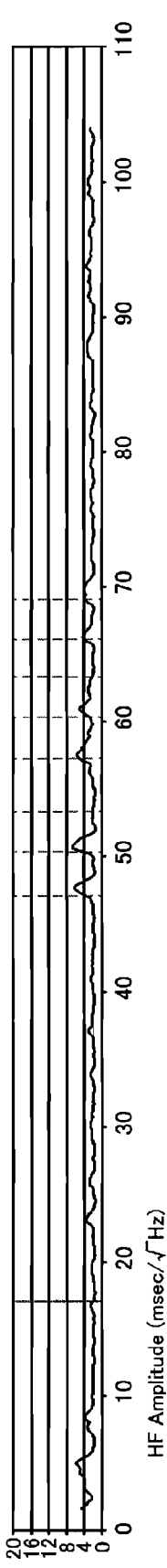

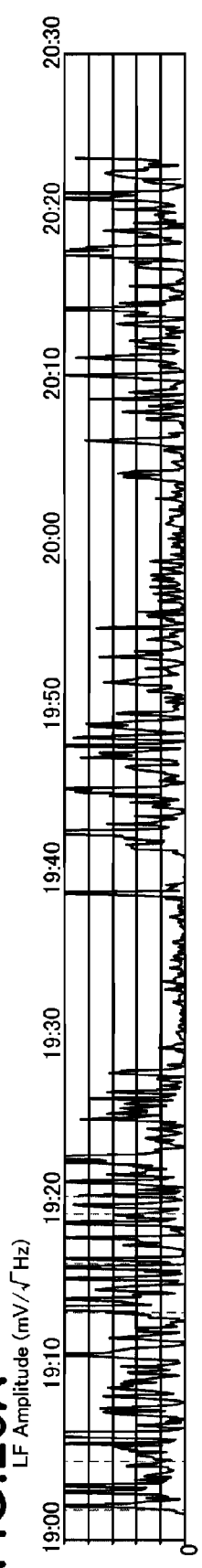
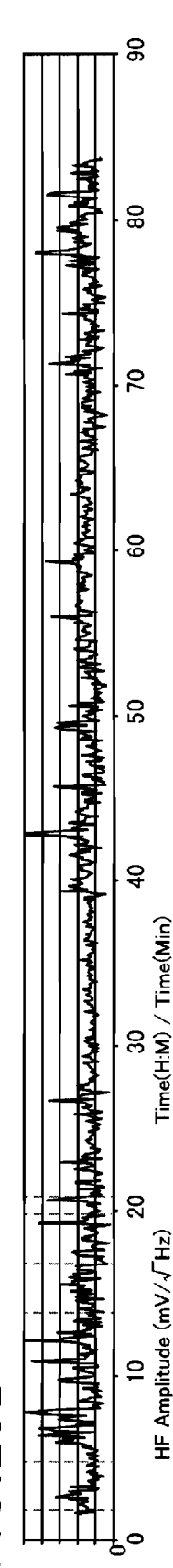
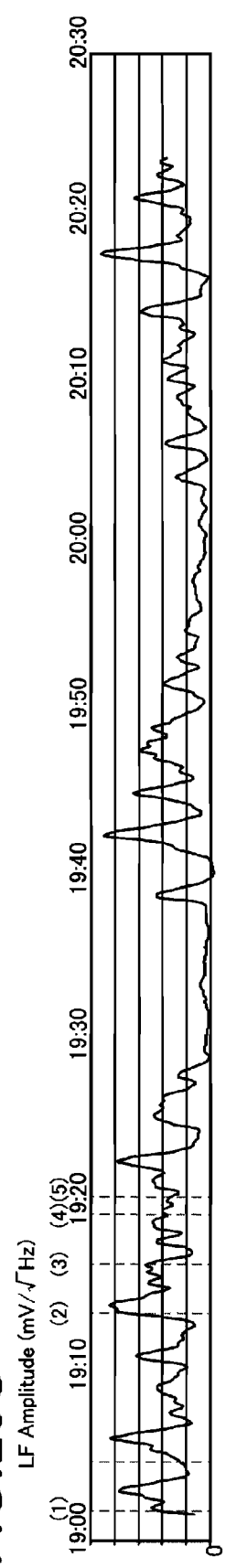
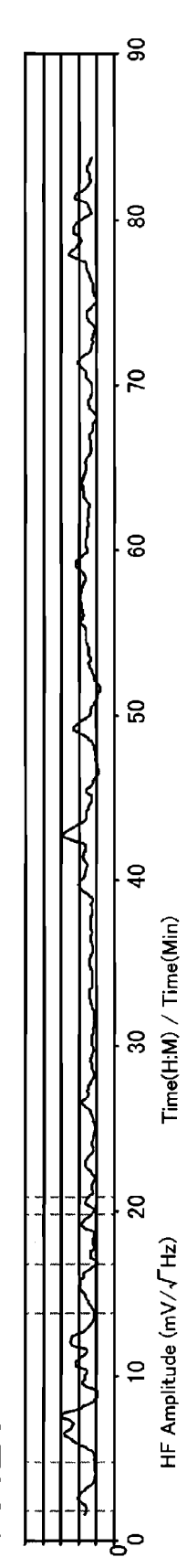
FIG.20A T WAVE PEAK VALUE
FIG.20B
FIG.20C
FIG.20D

PAIN JUDGING DEVICE TO JUDGE PAIN BASED ON A FREQUENCY COMPONENT OF A PEAK-RELEVANT VALUE

CROSS REFERENCE TO RELATED APPLICATIONS

This application is a national stage application under 35 U.S.C. 371 of PCT Application No. PCT/JP2009/002866 having an international filing date of 23 Jun. 2009, which designated the United States, which PCT application claimed the benefit of Japanese Application No. 2008-164466 filed 24 Jun. 2008, the entire disclosure of each of which are hereby incorporated herein by reference.

FIELD OF THE INVENTION

The present invention relates to a technique of objectifying the presence of pain.

BACKGROUND ART

If pain that a test subject has can be measured and objectively shown, it is possible to objectively measure the efficacy of a pain killer or visualize the pain of the test subject for an adequate medical treatment. Conventionally, as disclosed in, for example, Patent Document 1, a method of quantifying pain is used where the scale indicating the degree of pain is handed to a patient, the patient moves the cursor based on the degree of his or her pain, and the degree is read.
Patent Document 1: U.S. Pat. No. 6,258,042

SUMMARY OF THE INVENTION

Problem to be Solved by the Invention

However, since the conventional technique of measuring pain is based on the self-reported pain by a patient, there is a problem that it is difficult to acquire objective data.

It is therefore an object of this invention to provide a technique of solving the above problem and objectively judging pain.

Means for Solving the Problem

Each independent aspect of the present invention will be described below.

(1) A pain judging device according to the present invention comprises: an electrocardiographic information acquiring unit for acquiring electrocardiographic information measured in a measuring unit;
pain judging means for judging pain based on fluctuation related to a peak-relevant value of the electrocardiographic information; and
outputting means for outputting a judgment result by the pain judging means.

Consequently, it is possible to objectively judge the pain.

(2) With the pain judging device according to the present invention, the fluctuation related to the peak-relevant value is fluctuation of a characteristic value of a P wave, a Q wave, an R wave, an S wave, a T wave, or an ST.

Consequently, it is possible to accurately judge the pain based on these values of clear characteristic points.

(3) In the pain judging device according to the present invention, the pain judging means comprises noise eliminating means for improving an accuracy of pain judgment based on the fluctuation related to the peak-relevant value.

Consequently, it is possible to reduce error judgment that there is pain when there is no pain.

(4) In the pain judging device according to the present invention, the noise eliminating means eliminates influence of the noise using, as an index, fluctuation of an interval between characteristic points of the electrocardiographic complex, myoelectric information or a skin resistance or a skin potential measured by a second measuring unit.

Consequently, it is possible to further accurately prevent error judgment.

(5) In the pain judging device according to the present invention, the pain judging means comprises: a peak-relevant value frequency analyzing means for analyzing a frequency of the peak-relevant value acquired as time-series data; and a peak-relevant value LF component calculating means for calculating, as a peak-relevant value LF component, an LF component based on a frequency component of a peak-relevant value acquired by the peak-relevant value frequency analyzing means, and wherein the peak-relevant value LF component is acquired as characteristics of fluctuation of a peak-relevant value.

Consequently, it is possible to judge the pain by observing a peak-relevant value LF component.

(6) In the pain judging device according to the present invention, the pain judging means judges that there is pain when the peak-relevant value LF component increases.

Consequently, it is possible to further accurately judge the pain.

(7) In the pain judging device according to the present invention, the pain judging means comprises: interval frequency analyzing means for analyzing a frequency of an interval between waveform characteristic points of the electrocardiographic information acquired as time-series data; and interval HF component calculating means for calculating, as an interval HF component, an HF component based on a frequency component of the interval between the waveform characteristic points acquired by the interval frequency analyzing means, and wherein the interval HF component is acquired as characteristics of fluctuation of an interval.

Consequently, it is possible to increase the accuracy of pain judgment by observing the interval HF component.

(8) With the pain judging device according to the present invention, the interval HF component is an index indicating a respiratory fluctuation component acquired from a frequency component of an interval between waveform characteristic points acquired by the interval frequency analyzing means.

(9) In the pain judging device according to the present invention, the pain judging means judges that there is pain when an interval HF component does not decrease and a peak-relevant value LF component increases.

Consequently, it is possible to further accurately judge the pain.

(10) In the pain judging device according to the present invention, the pain judging means comprises: peak-relevant value frequency analyzing means for analyzing a frequency of the peak-relevant value acquired as time-series data; and peak-relevant value HF component calculating means for calculating as a peak-relevant value HF component an HF component based on a frequency component of a peak-relevant value acquired by the peak-relevant value frequency analyzing means, and wherein the peak-relevant value HF component is acquired as characteristics of fluctuation of a peak-relevant value.

(11) In the pain judging device according to the present invention, the pain judging means judges that there is pain when an interval HF component does not decrease and both of a peak-relevant value LF component and a peak-relevant value HF component increase.

Consequently, it is possible to more accurately judge the pain.

The "electrocardiographic complex measuring unit" of this invention refers to a unit with the function of measuring an electrocardiographic complex of a measurement target, and corresponds to an electrocardiographic meter etc. In the embodiment, this corresponds to ECG electrodes 20 and an amplifier 22 of FIG. 2.

In the embodiment, the "pain judging means" corresponds to steps S3 to S7 of FIG. 3, and steps S8 to S14 of FIG. 4.

In the embodiment, the "interval frequency analyzing means" corresponds to steps S5 and S6 of FIG. 3.

In the embodiment, the "interval waveform HF component calculating means" corresponds to step S7 of FIG. 3.

In the embodiment, the "peak-relevant value frequency analyzing means" corresponds to steps S8 and S9 of FIG. 4.

In the embodiment, the "peak-relevant value LF component calculating means" corresponds to step S10 of FIG. 4.

The "outputting means" refers to means having function of outputting a judgment result in some form, and is a concept that includes a unit outputting the result to, for example, a display, a printer, another computer, or recording medium or that includes a communication unit for transmitting the result.

The "electrocardiographic information" is a concept that includes not only electrocardiographic complex data but also, for example, a value of a characteristic portion of the electrocardiographic complex.

The "peak-relevant value" is a concept that includes not only a peak (crest) value but also a value related to a waveform such as an average peak value or waveform area.

The "electrocardiographic information acquiring unit" is a concept that includes a circuit for receiving signals from the measuring unit, a drive for reading data from the recording medium, and a receiving unit for receiving data transmitted via communication.

The "fluctuation" refers to temporal fluctuation of a value.

The "fluctuation of a characteristic value of a P wave, Q wave, R wave, S wave, T wave, or ST" refers to fluctuation of a characteristic value (for example, a peak value or average value) that characterizes the P wave etc.

The "program" is a concept that includes not only a program that can be directly executed by the CPU but also a program in a source form, a compressed program, and an encrypted program.

BRIEF DESCRIPTION OF THE DRAWINGS

FIG. 6a shows data of each pulse recorded on a hard disc 32.

FIG. 6b shows average data of five-second periods that are recorded on the hard disc 32.

FIG. 9 shows data measured by the pain judging device.

FIG. 10 shows data measured by the pain judging device.

FIGS. 15A-15D show changes in an LF component and HF component of a T wave peak value.

FIGS. 16A-16D show changes in an LF component and HF component of an ST value.

FIGS. 17A-17D show changes in an LF component and HF component of a QRS interval.

FIGS. 20A-20D show changes in a T wave peak value LF component and T wave peak value HF component when a pain killer is administered.

EMBODIMENT FOR CARRYING OUT THE INVENTION

1. Functional Block Diagram

Figure 1:
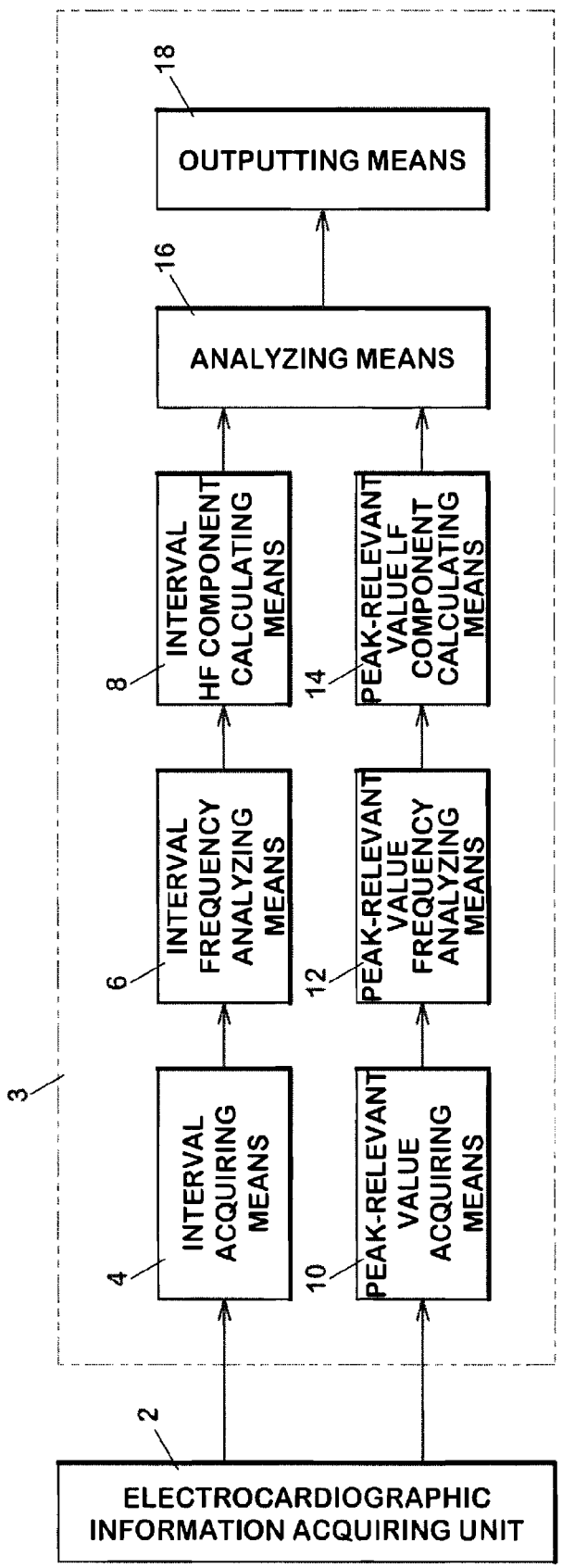
FIG. 1 is a functional block diagram of a pain judging device according to an embodiment of the present invention.

FIG. 1 is a functional block diagram of a pain judging device according to an embodiment of the present invention. An electrocardiographic information acquiring unit 2 acquires electrocardiographic information of a target.

Peak-relevant value acquiring means 10 acquires a peak-relevant value (for example, a peak value of an R wave (i.e. R wave peak value)) per cycle based on the acquired electrocardiogram. The peak-relevant value acquiring means 10 may acquire data that includes a peak-relevant value in advance or acquire this data by calculating the peak-relevant value based on electrocardiographic data. The peak-relevant value frequency analyzing means 12 analyzes the frequency of the peak-relevant value acquired as time-series data, and acquires the magnitude of each frequency component. The peak-relevant value LF calculating means 14 calculates an LF component (i.e. peak-relevant value LF component) based on the frequency component of the peak-relevant value.

Interval acquiring means 4 acquires an interval between characteristic points of an electrocardiographic complex (for example a time interval between R waves (i.e. RR interval)) based on the acquired electrocardiogram. Note that the interval acquiring means 4 may acquire data that includes the interval between the characteristic points in advance, or acquire this data by calculating the interval between the characteristic points based on the electrocardiographic data. Interval frequency analyzing means 6 analyzes the frequency of the interval between the characteristic points acquired as the time-series data, and acquires the magnitude of each frequency component. Interval HF component calculating means 8 calculates an HF component (i.e. interval HF component) based on the frequency component of the interval between the characteristic points acquired by the interval frequency analyzing means 6.

Analyzing means 16 judges the presence or absence of pain and the degree of pain as follows based on changes in the peak-relevant value LF component and the interval HF component. The analyzing means 16 judges pain based on the peak-relevant value LF component. When the peak-relevant value LF component is greater than usual, there is a possibility of pain. Further, when the peak-relevant value LF component is the same as or less than usual, there is no possibility of pain.

However, even when the peak-relevant value LF component is greater than usual and there is a possibility of pain, if the interval HF component is less than usual, the analyzing means 16 does not judge that there is pain. When the peak-relevant value LF component is greater than usual and the interval HF component is the same as or greater than usual, the analyzing means 16 judges that there is pain. At this time, the analyzing means 16 judges the degree of the peak of the peak-relevant value LF component as the degree of pain.

In this embodiment, pain judging means 3 includes the peak-relevant value acquiring means 10, peak-relevant value frequency analyzing means 12, peak-relevant value LF component calculating means 14, interval acquiring means 4, interval frequency analyzing means 6, and interval HF component calculating means 8. Further, the noise canceling means includes the interval calculating means 4, interval frequency analyzing means 6, and interval HF calculating means 8.

The outputting means 17 outputs a judgment result of pain that is analyzed as described above, to, for example, a display.

2. Hardware Configuration

Figure 2:
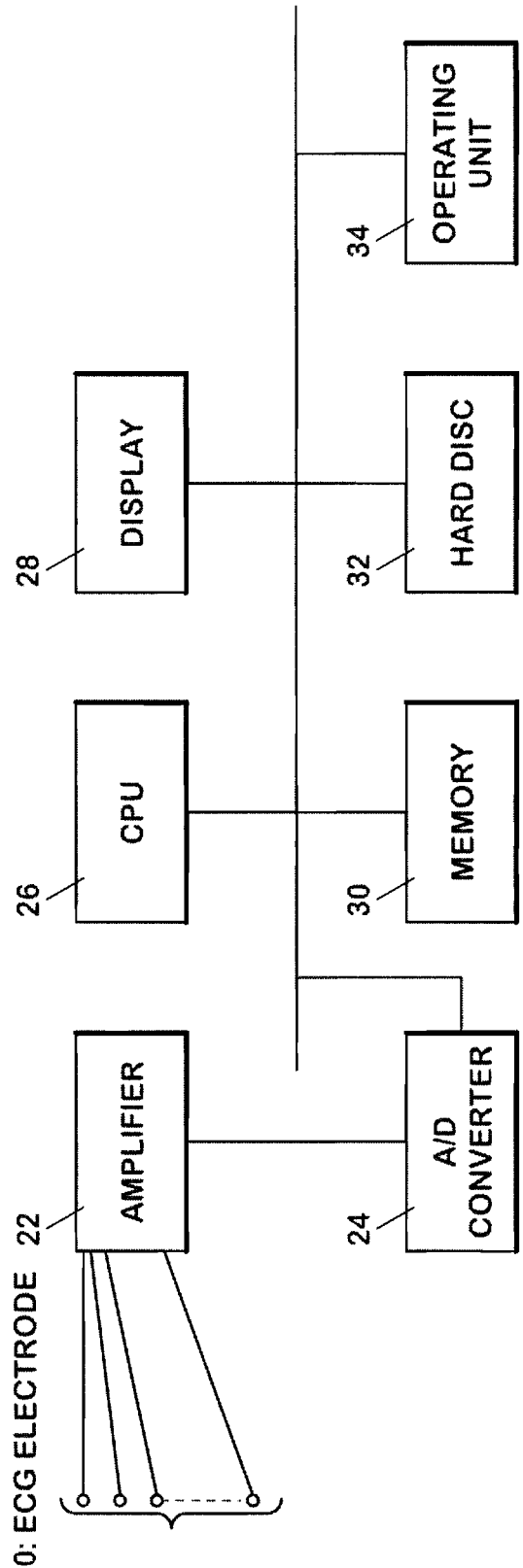
FIG. 2 shows a hardware configuration when a pain judging device is realized using a CPU.

FIG. 2 shows a hardware configuration when the pain judging device according to an embodiment is realized using a CPU 26. The CPU 26 is connected with an A/D converter 24, a display 28, a memory 30, a hard disc 32, and an operating unit 24.

ECG electrodes 20 are attached to the body of a target (a test subject) to acquire electrocardiographic signals of the target. The electrocardiographic signals from the ECG electrodes 20 are amplified by the amplifier 22 and are converted into electrocardiographic complex signals of digital data by the A/D converter 24. The A/D converter 24 stores the generated digital data in the memory 30.

The memory 30 is used as a work area of the CPU 26. The display 28 displays, for example, a judgment result. The operating unit 34 includes a button and the like for inputting an operation by an operator. A program for judging pain is stored in the hard disc 32.

3. Processing of the Pain Determining Program

Figure 3:
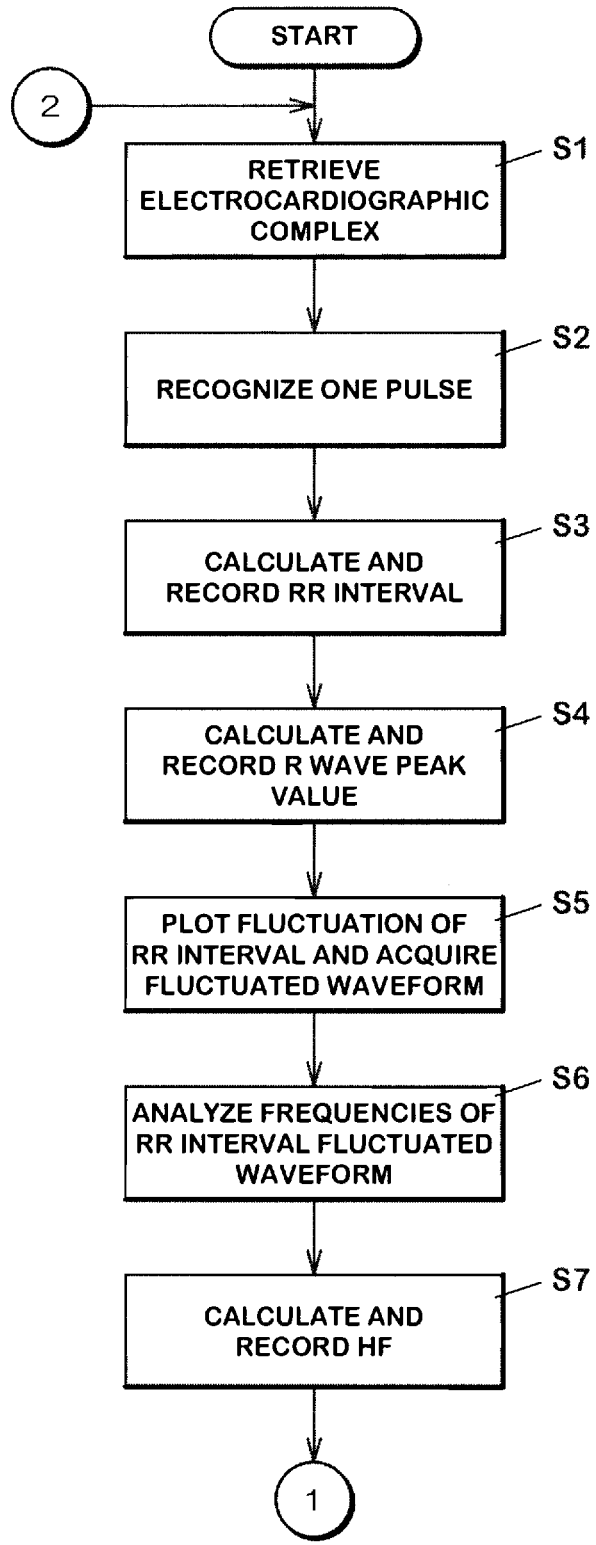
FIG. 3 is a flowchart of a pain judging program.
Figure 4:
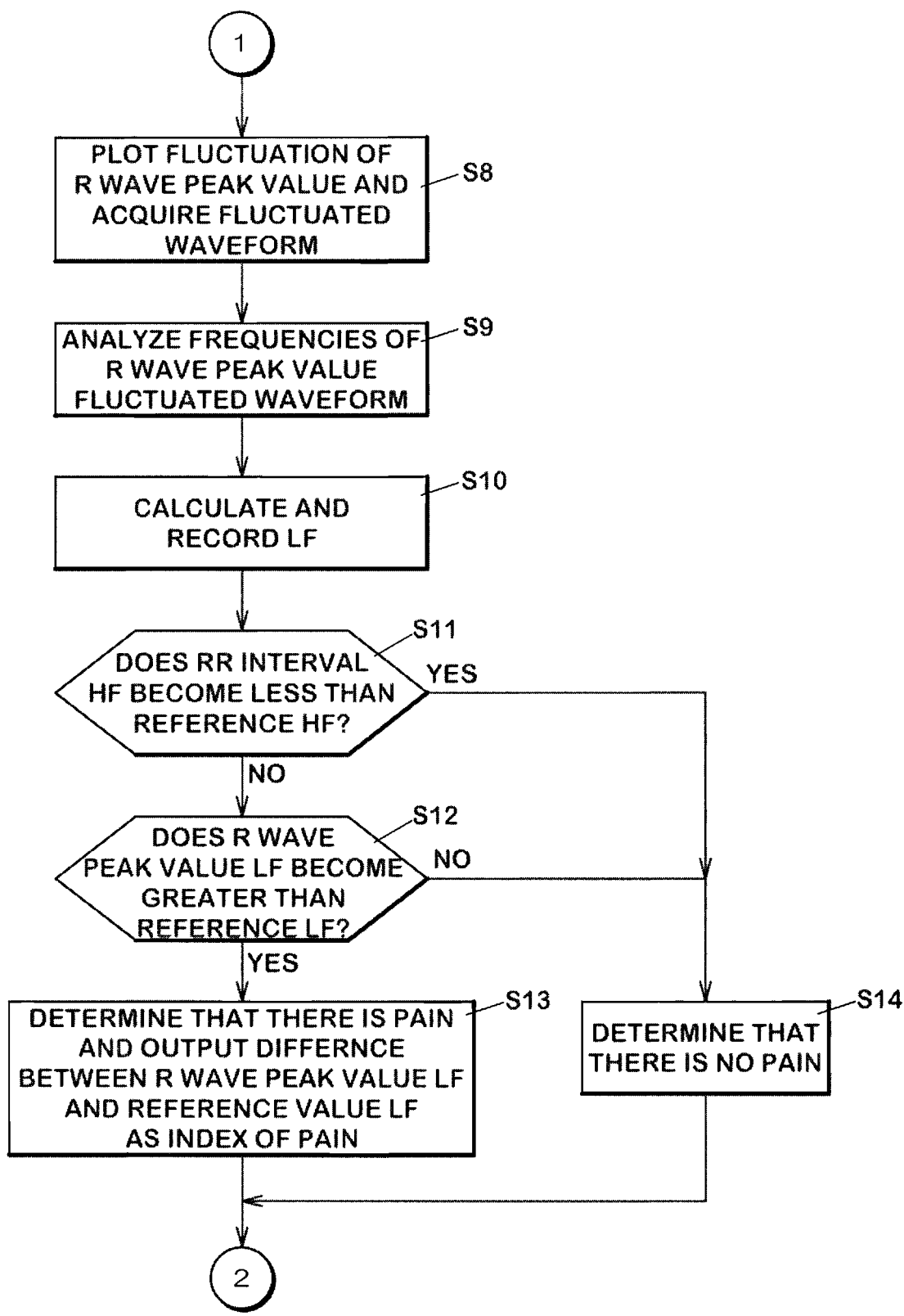
FIG. 4 is a flowchart of a pain judging program.
Figure 5:
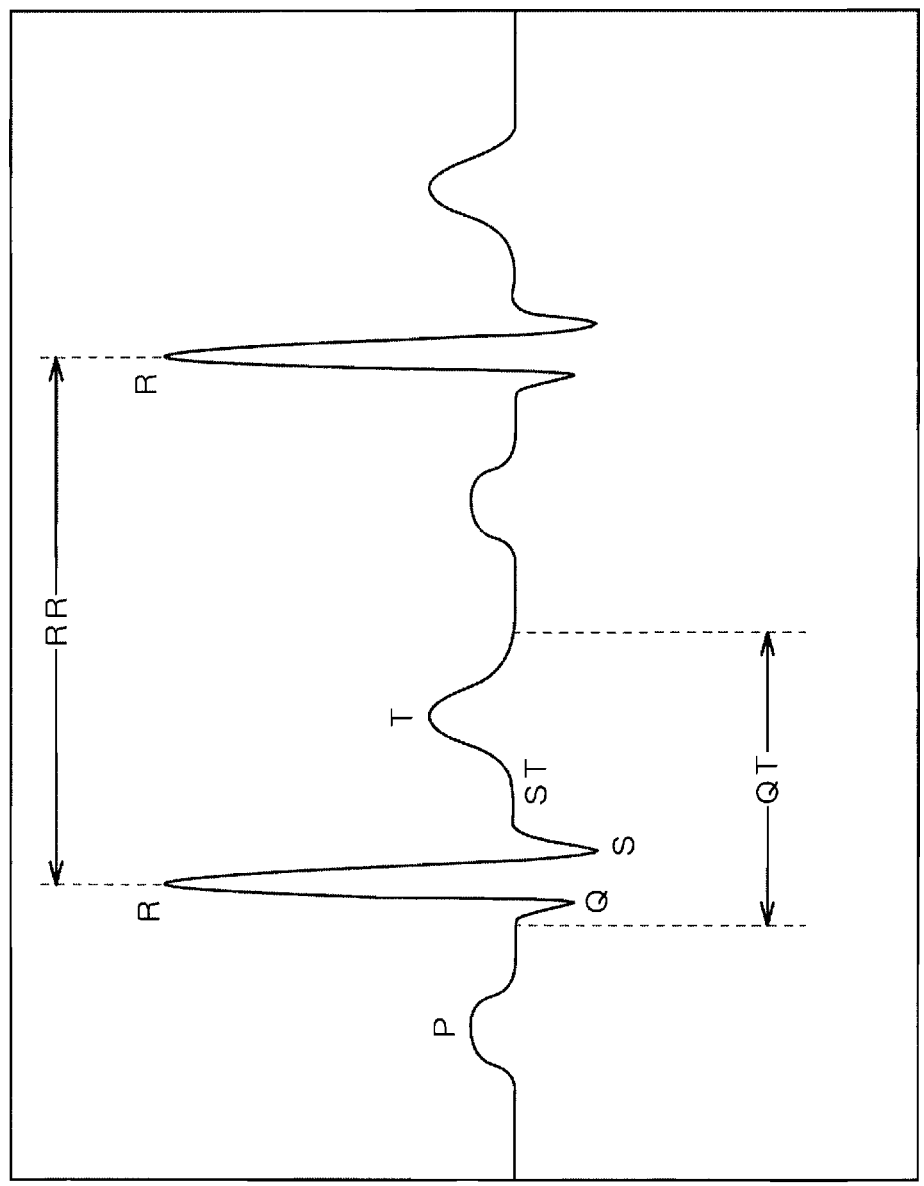
FIG. 5 shows an electrocardiographic complex.

FIG. 3 shows the flowchart of the pain judging program stored on the hard disc 32. In step S1, the CPU 26 retrieves electrocardiographic complex data recorded in the memory 30. The electrocardiographic complex is digital data obtained by sampling changes in a potential at each predetermined time, and is schematically shown in FIG. 5.

The CPU 26 recognizes a pulse of the retrieved electrocardiographic complex (step S2). For example, the CPU 26 recognizes a wave with a peak that exceeds a predetermined value as an R wave. Then, the CPU 26 recognizes a bottom wave immediately before this R wave as a Q wave, and recognizes the start point of the Q wave as the start point of a pulse. In the same fashion, the CPU 26 recognizes each pulse by recognizing the start point of the next pulse. Further, the CPU 26 recognizes the bottom wave immediately after the R wave as an S wave, and recognizes a flat portion subsequent to the end of the S wave as an ST portion.

Next, the CPU 26 calculates the time interval between the peak of the R wave of the pulse that is recognized this time and the peak of the R wave of the previous pulse, and stores it on the hard disc 32 (step S3). In this embodiment, step S3 corresponds to the interval acquiring means. Further, the value of the peak of the R wave is calculated, and is stored on the hard disc 32 (step S4). In this embodiment, step S4 corresponds to the peak-relevant value acquiring means. Consequently, when processing continues, as shown in FIG. 6a, the RR interval and the R wave peak value of each pulse are stored on the hard disc 32.

In FIG. 6a, R indicates the R wave peak value and RR indicates the RR interval. Further, the absolute time indicates the measured time, and the relative time indicates elapsed time from the start time of measurement which is zero elapsed time. Furthermore, in this embodiment, as shown in FIG. 6a, characteristic values other than the RR interval and the R wave peak value are also recorded. P indicates a P wave peak value, Q indicates a Q wave peak value, S indicates an S wave peak value, ST indicates an ST value, T indicates a T wave peak value, PR indicates an interval between the P wave and the R wave, VAT indicates an interval between the Q wave and the R wave, QRS indicates an interval between the Q wave and the S wave and QT indicates an interval between the Q wave and the T wave.

Figure 7A:
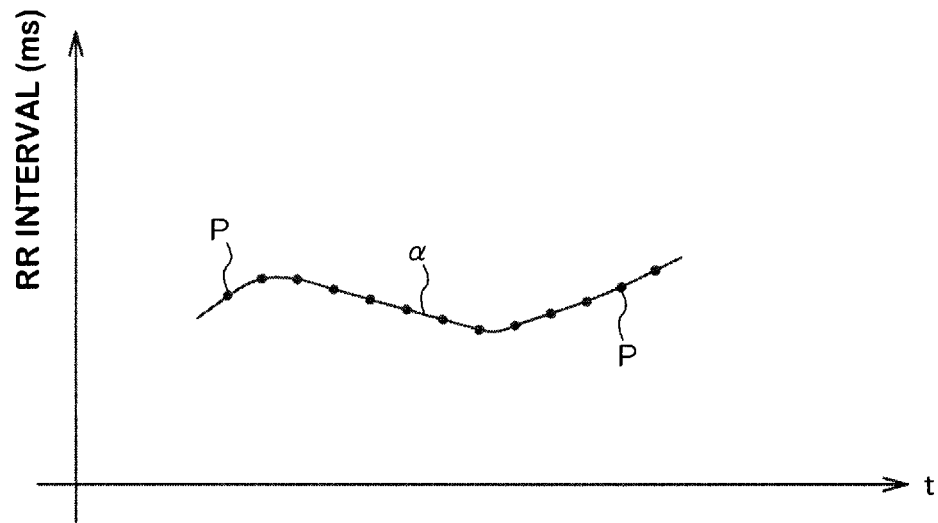
FIGS. 7A-7B show spline interpolation of an RR interval and R wave peak value.

Next, the CPU 26 calculates the waveform that represents temporal fluctuation of the RR interval (step S5). For example, as shown in FIG. 6b, the CPU 26 calculates temporal fluctuation of the average value of the RR interval of five seconds based on data shown in FIG. 6a. Next, as shown in FIG. 7A, on a plane where the horizontal axis represents time and the vertical axis represents the RR interval, temporal fluctuation of the average value of the RR interval of FIG. 6b is plotted as shown by P. The time interval plotted on the horizontal axis may correspond to the pulse duration. The temporal fluctuation of the RR interval is a discrete value of each pulse. Therefore, a smooth waveform a is generated by spline interpolation as shown in FIG. 7A.

Next, the CPU 26 performs resampling at a time interval shorter than one pulse (for example, several ten milliseconds) based on the generated RR interval fluctuated waveform a to obtain time-series data of the RR interval. The CPU 26 analyzes the frequency of this time-series data (by for example, Fourier transform, Wavelet transform, or the like), and calculates the value of each frequency component (step S6). The value resulting from this frequency analysis is calculated per unit time interval of resampling.

Figure 8:
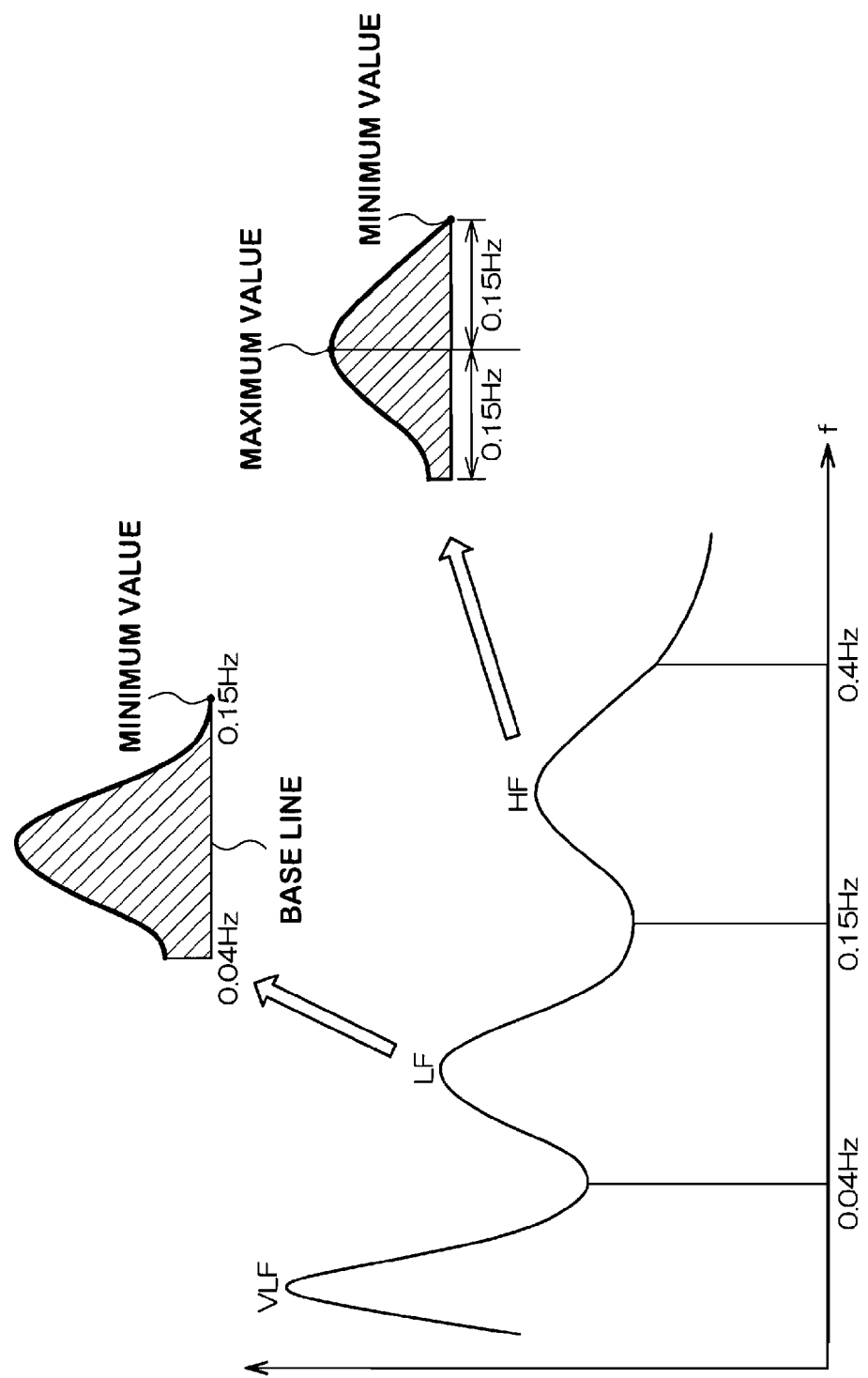
FIG. 8 shows calculation of an LF component and HF component.

FIG. 8 shows the waveform of frequency analysis obtained in this way. The vertical axis indicates the power spectrum density (where the unit is the square of $\mathrm{msec}^2 \times \mathrm{Hz}$), and the horizontal axis indicates the frequency (where unit is Hz). A wave with a peak appearing at a low frequency is referred to as "VLF," a wave appearing at a higher frequency is referred to as "LF", and a wave appearing at a much higher frequency is referred to as "HF" (representing a respiratory fluctuation component). The CPU 26 calculates the average value of the wave of HF.

In this embodiment, the CPU 26 calculates the average value of HF as follows. First, the CPU 26 finds the local maximum value between 0.15 Hz and 0.4 Hz (up to 2 Hz is also possible). Next, the CPU 26 extracts the waveform in the section 0.15 Hz before and after the frequency of the local maximum value, and calculates the area assuming the minimum value as the base line (see FIG. 8). The CPU 26 calculates the average value by dividing this area by the frequency width (0.3 Hz), and assumes this average value as an RR interval HF component (where the unit is m sec/(square root of Hz)).

The CPU 26 calculates the average value of the RR interval HF components which are calculated per unit time of resampling, of a five second period, and stores the average value on the hard disc 32 (step S7). FIG. 9 shows stored examples of the RR interval HF component. In this figure, the item indicated by HF Amplitude indicates the RR interval HF component.

Figure 7B:
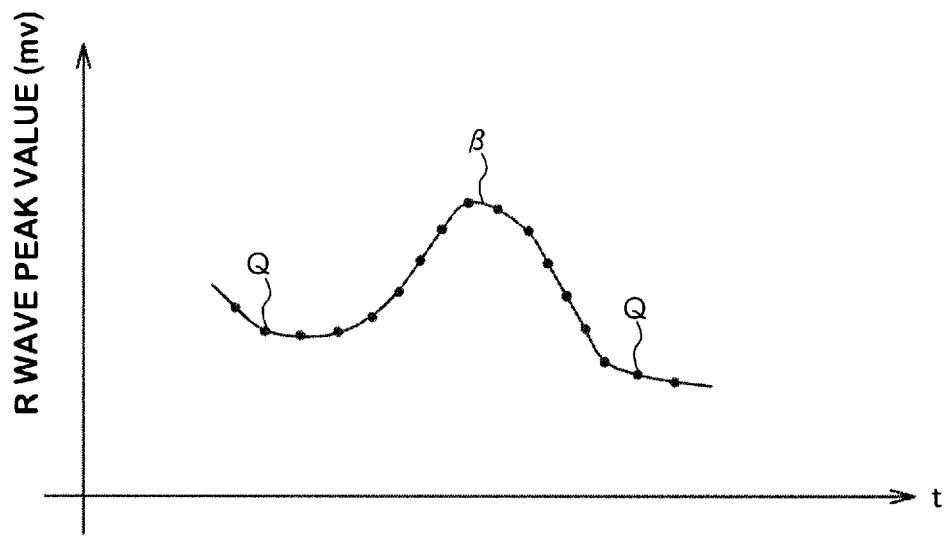

Next, the CPU 26 calculates the waveform that represents temporal fluctuation of the R wave peak value (step S8). For example, as shown in FIG. 7B, on a plane where the horizontal axis represents time and the vertical axis represents the R wave peak value, temporal fluctuation of the average value of the R wave peak value in the five-second period is plotted as shown by Q based on the data in FIG. 6b. The time interval that is plotted on the horizontal axis may correspond to time of an actual pulse. The temporal fluctuation of the R wave peak value is a discrete value of each pulse. Therefore, a smooth waveform β is generated by spline interpolation as shown in FIG. 7B.

Next, the CPU 26 performs resampling at a time interval shorter than one pulse (for example, several ten milliseconds) based on the generated R wave peak value waveform β to obtain the time-series data of the R wave peak value. The CPU 26 analyzes the frequency of this time-series data (by for example, Fourier transform, Wavelet transform, or the like), and calculates the value of each frequency component (step S9). The value resulting from this frequency analysis is calculated per unit time interval of resampling.

FIG. 8 shows the waveform of the frequency analysis obtained in this way. For the frequency analysis waveform of the R wave peak value which is the time-series data, the CPU 26 calculates an R wave peak value LF component according to the calculating method which is the same as the method applied to the above RR interval HF component.

In this embodiment, the CPU 26 calculates the average value of the R wave peak value LF as follows. First, the CPU 26 extracts the waveform in the section between 0.04 Hz and 0.15 Hz, and calculates the area assuming the minimum value as the base line (see FIG. 8). The CPU 26 calculates the average value by dividing this area by the frequency width (0.11 Hz), and assumes this average value as the R wave peak value LF component (where the unit is m sec/(square root of Hz)).

The CPU 26 calculates the average value of the R wave peak value HF component of the five-second periods calculated per unit time of resampling, and stores the average value on the hard disc 32 (step S10). FIG. 10 shows stored examples of the R wave peak value LF component. In this figure, the item indicated by LF Amplitude indicates the R wave peak value LF component.

Next, the CPU 26 judges whether or not the RR interval HF component (i.e. the above average value in the five-second period) which is the judgment target decreases from the reference HF component (step S11). Here, the reference HF component is the RR interval HF component when the target is in the normal state. The value measured in advance may be stored as the reference HF component, and the average value of the RR interval HF component over a predetermined time in this measurement may be used. The same applies to the reference LF component described later. When the RR interval HF component is less than the reference HF component, it is judged that there is no "pain" at this pulse.

When the RR interval HF component is at the same level as or greater than the reference HF component, the CPU 26 judges whether or not the R wave peak value LF component which is the judgment target becomes greater than the reference LF component (step S12). When the R wave peak value LF component does not become greater the reference LF component, it is judged that there is no "pain" (step S14). When the R wave peak value LF component becomes greater than the reference LF component, it is judged that there is "pain." As an index of pain, the CPU 26 outputs (display on the display 28, for example) the value obtained by subtracting the reference LF component from the R wave peak value LF component. For example, the R wave peak value LF component may be 0.04 mV/Hz$^{1/2}$, and the R wave peak value HF component may be 0.03 mV/Hz$^{1/2}$.

When the above processing is finished, the step returns to step S1 and the next processing is executed. In this way, the presence or absence of pain is detected in real-time.

FIG. 11 and FIG. 12 show examples of measuring pain as described above. FIG. 11A shows a graph showing the transition of the R wave peak value LF component (i.e. average in five seconds). In FIG. 11, the broken lines of (1) to (8) indicate that the following events have occurred. In (1), (2) and (4), the shin is sandwiched with a clip and given pain stimulation. In (5), (7), and (8), the nail is sandwiched with a clip and given pain stimulation. In (3) and (6), no pain stimulation is given. As is clear from this graph, immediately after (1), (2), (4), (5), (7), and (8) where pain is given, the increase in the R wave peak value LF component is observed. Accordingly, by observing the R wave peak value LF component, it is possible to judge pain.

Figure 12A:
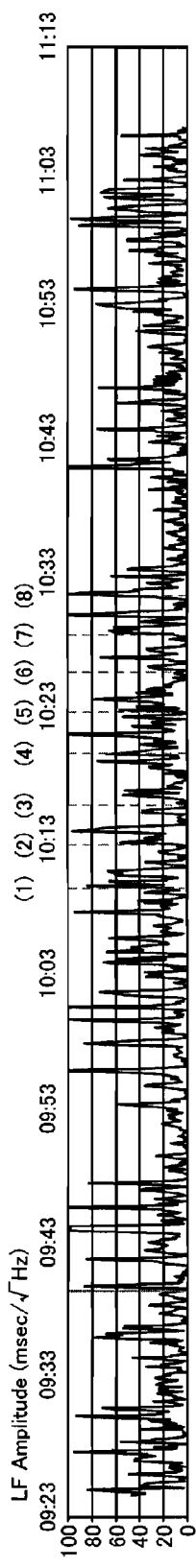
FIGS. 12A-12D show a graph of data measured by the pain judging device.
Figure 12B:
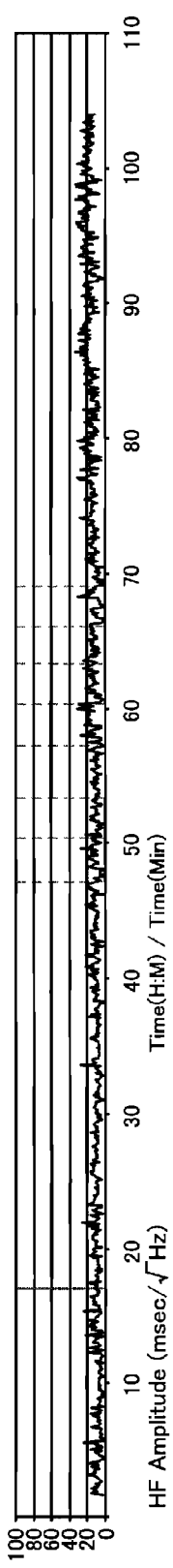
Figure 12C:
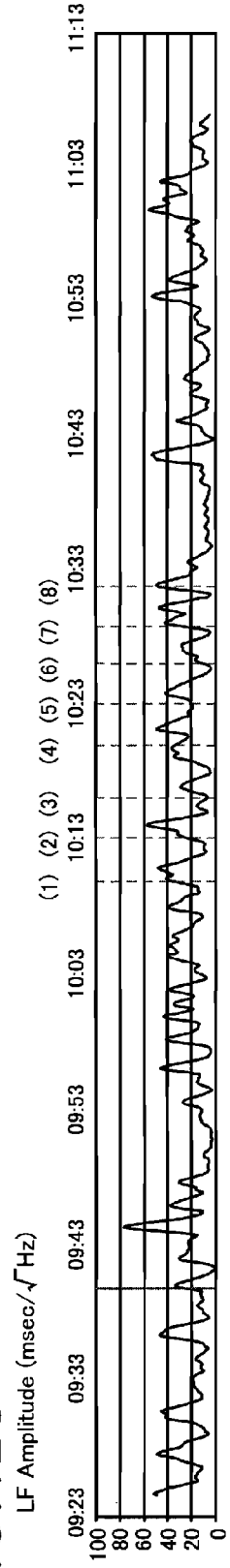

However, even immediately after (3) and (6) where no pain is given, the increase in the R wave peak value LF component is observed although the level is low. Then, in this embodiment, by taking the RR interval HF component into account, the accuracy of judgment is improved. That is, when both of the R wave peak value LF component and the RR interval HF component increase, it is judged that there is pain. FIG. 12B shows the RR interval HF component. As is obvious from this figure, immediately after (3) and (6) where no pain is given, the increase in the RR interval HF component is not observed. Accordingly, it is possible to judge that there is pain in (1), (2), (4), (5), (7), and (8). On the contrary, (3) and (6) do not meet the above condition, and it is possible to judge that there is no pain.

Although pain is artificially given and measured above, an effect is measured below when a pain killer is administered to a patient having constant pain due to a cancer.

FIG. 18 is the graph showing the relationship between the R wave peak value LF component before and after administration of morphine hydrochloride salt as a pain killer and pain complained by a patient of the pharynx cancer. From the start of measurement (1) to the time when the patient complains severe pain (2), the R wave peak value LF component transitions at a high level. At time (3), the patient makes a nurse call, and, even at time (4), complains severe pain. At time (5), an oral solution (i.e. morphine hydrochloride) as a pain killer is administered. This oral solution stimulates the throat significantly and causes pain when this solution is swallowed. Therefore, pain is caused after the solution is taken.

A little after time (5) when the pain killer is administered in FIG. 18, the R wave peak value LF component decreases, and this matches with the patient's complaint that pain is eased. Further, the decrease in the R wave peak value HF component is not observed.

FIG. 19 is a graph of the RR interval HF component in the above experiment. Subsequent to time (5) after the pain killer is administered, the RR interval HF component does not increase on average.

FIG. 20 is the graph of the T wave peak value LF component and T wave peak value HF component in the above experiment. These components are observed to have the same inclination as the R wave peak value LF component and the R wave peak value HF component.

4. Other Embodiment (1) With the above embodiment, although the average values of the R wave peak value LF component and the RR interval HF component over a predetermined time (i.e. the above average in five seconds in the embodiment), judgment may be made by using the R wave peak value LF component and the RR interval HF component as is.

Figure 11A:
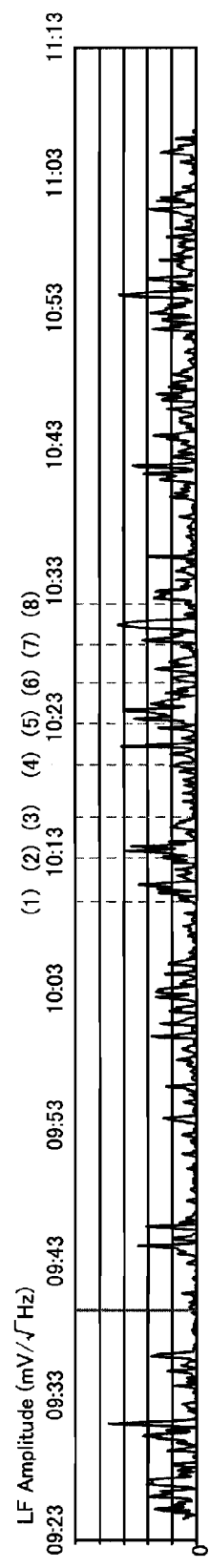
FIGS. 11A-11D show a graph data measured by the pain judging device.
Figure 11B:
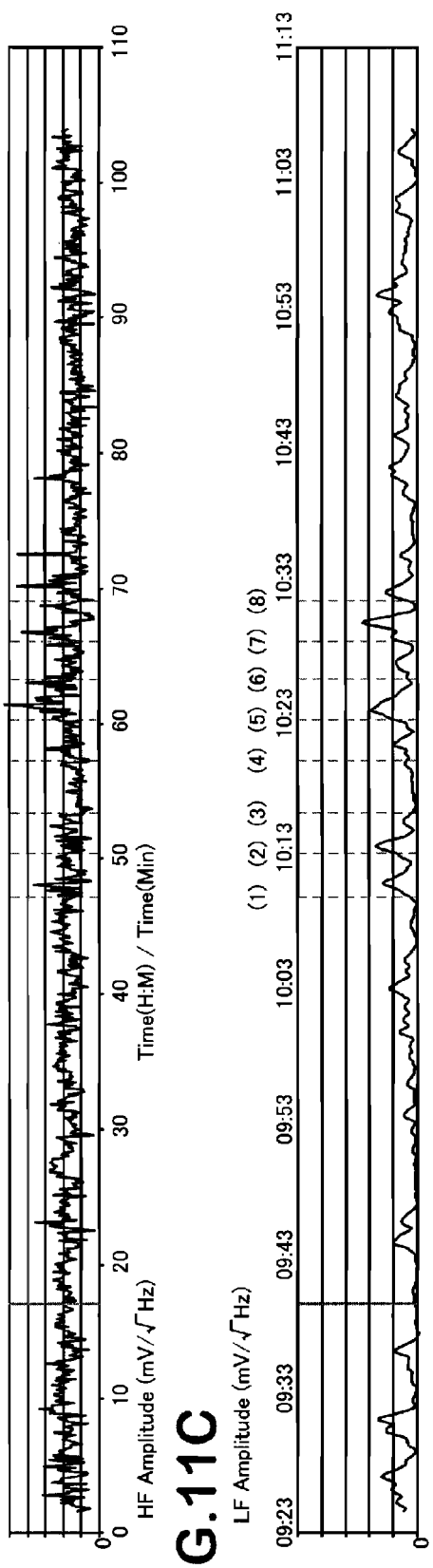
Figure 11C:
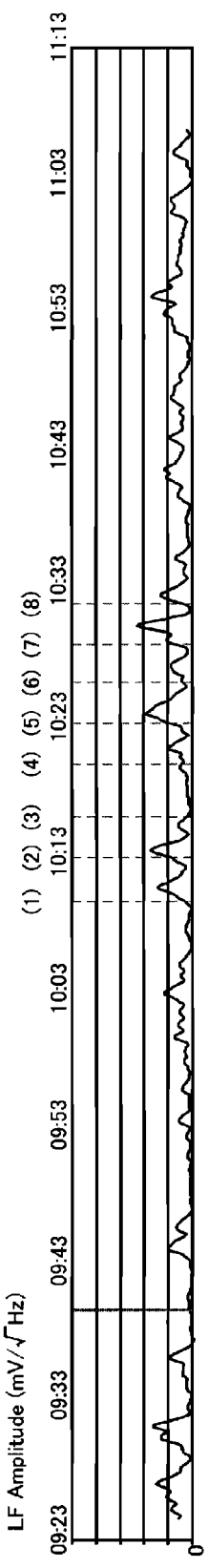
Figure 11D:
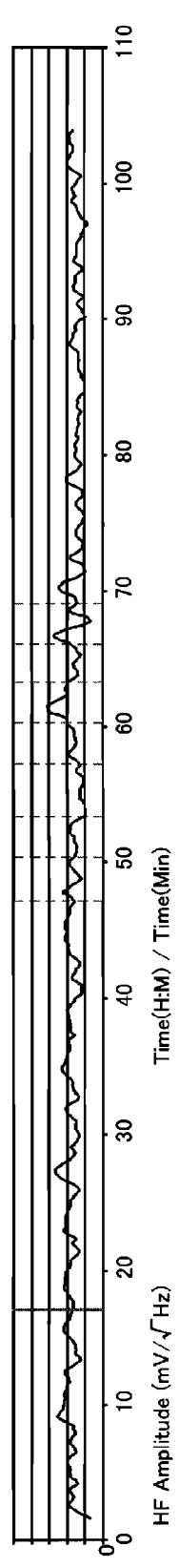
Figure 12D:
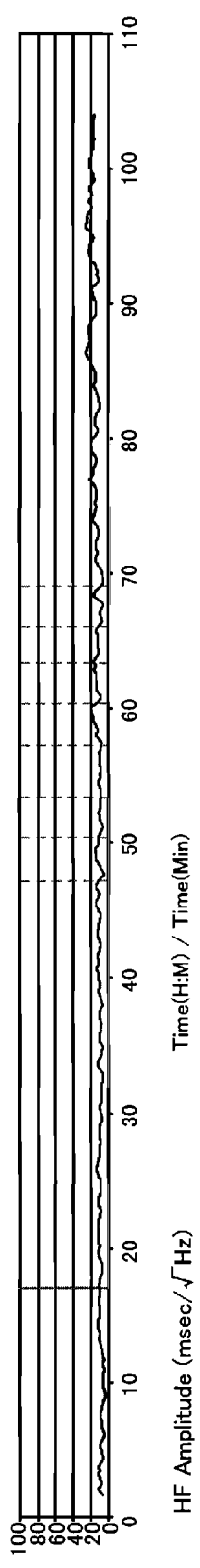
Figure 13A:
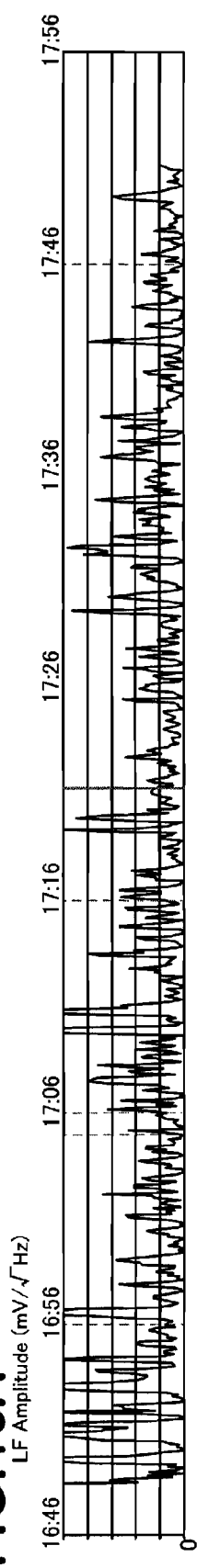
FIGS. 13A-13D show a graph of data measured by the pain judging device.
Figure 13B:
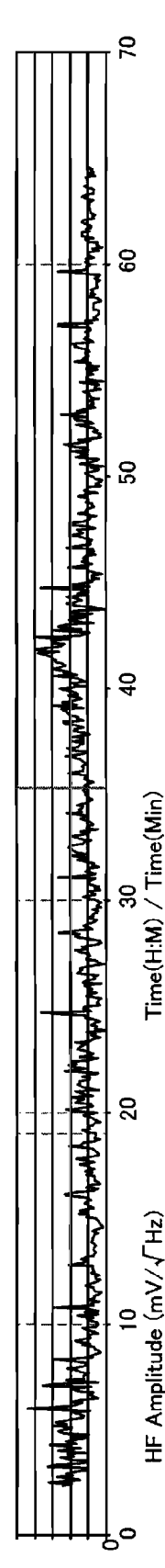
Figure 13C:
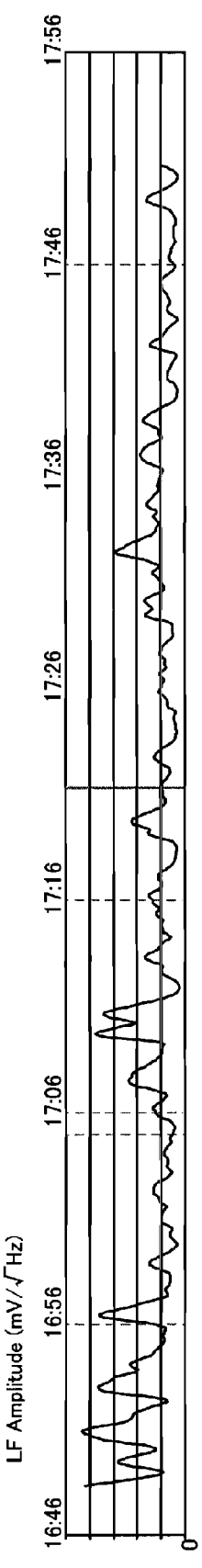
Figure 13D:
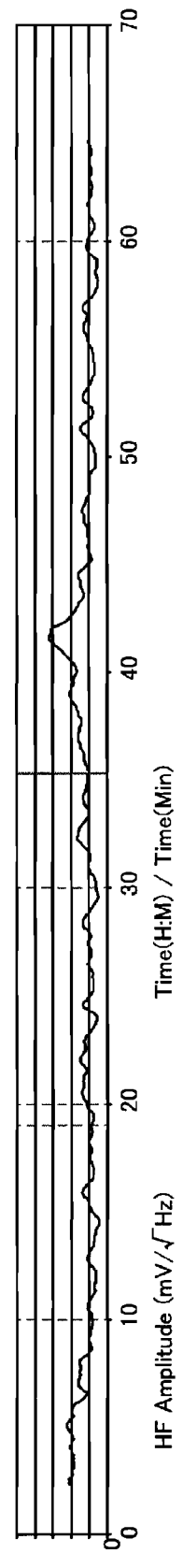
Figure 14A:
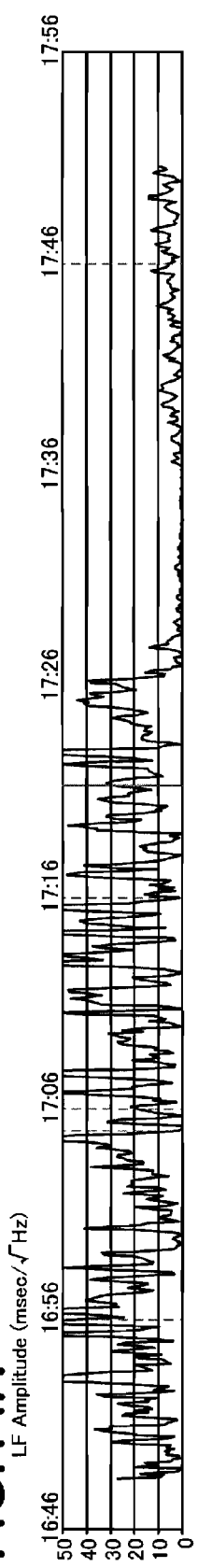
FIGS. 14A-14D show a graph of data measured by the pain judging device.
Figure 14B:
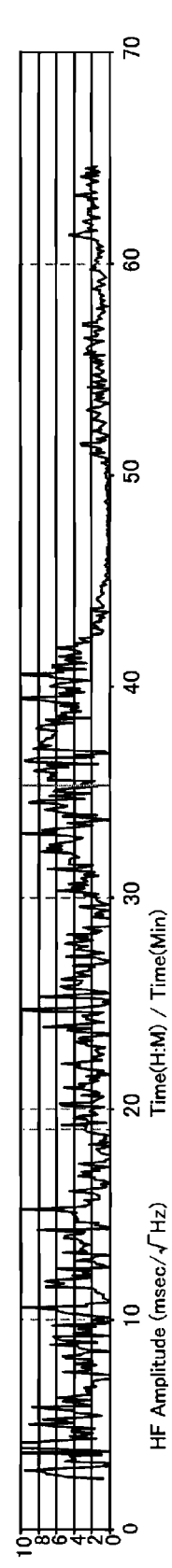
Figure 14C:
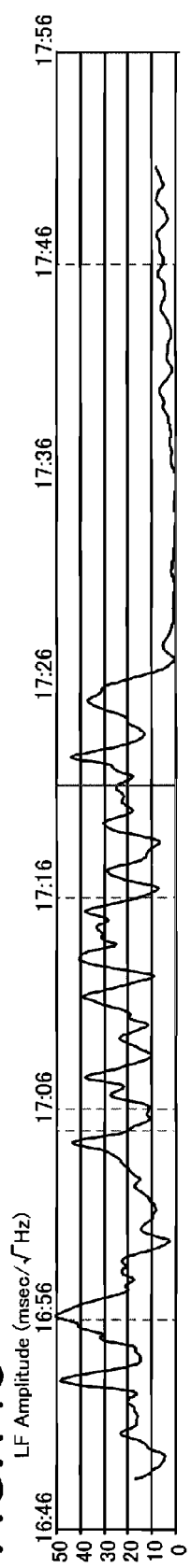
Figure 14D:
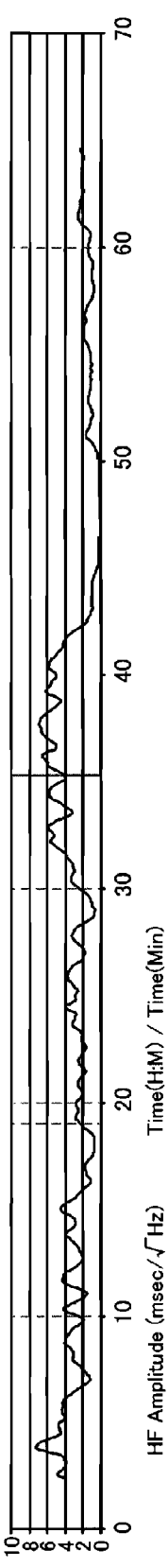
Figure 18A:
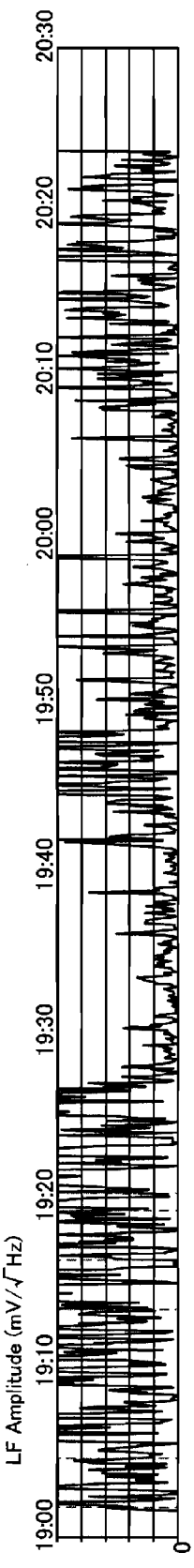
FIGS. 18A-18D show changes in an R wave peak value LF component and R wave peak value HF component when a pain killer is administered.
Figure 18B:
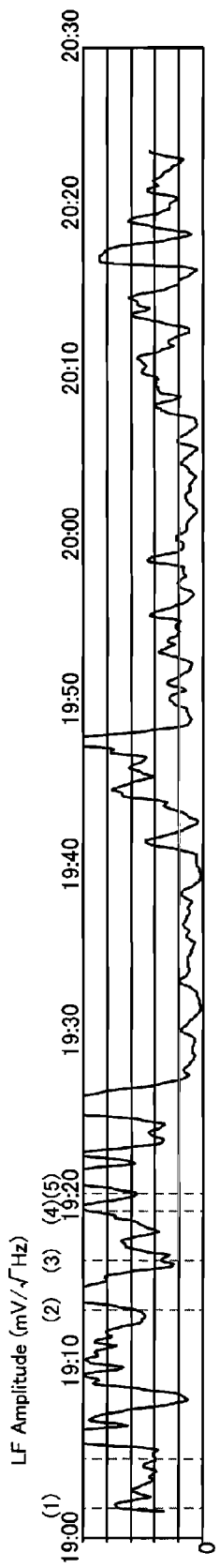
Figure 18C:
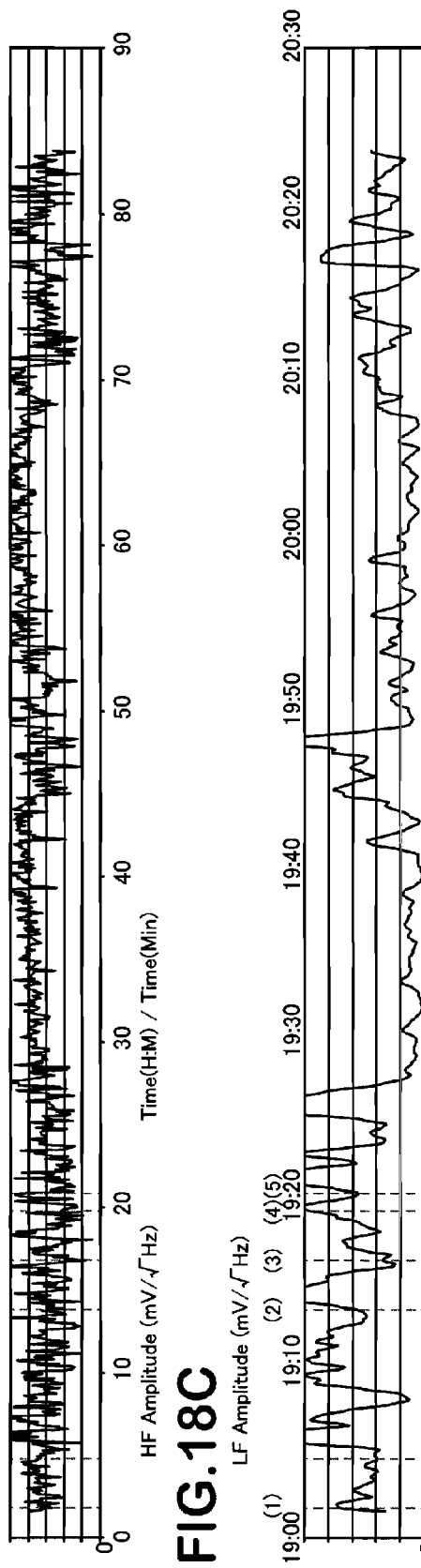
Figure 18D:
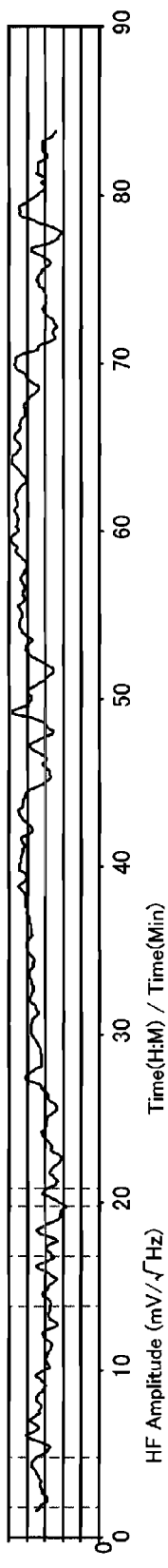
Figure 19A:
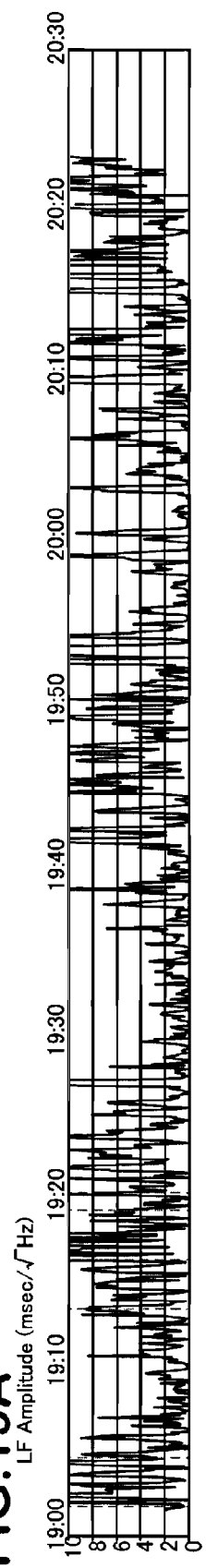
FIGS. 19A-19D show changes in an RR interval HF component when a pain killer is administered.
Figure 19B:
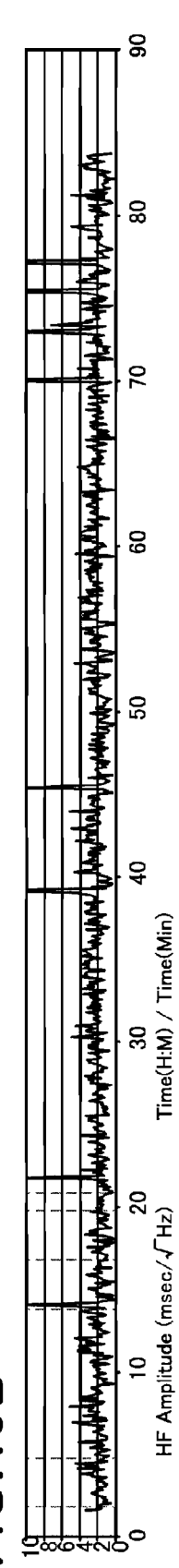
Figure 19C:
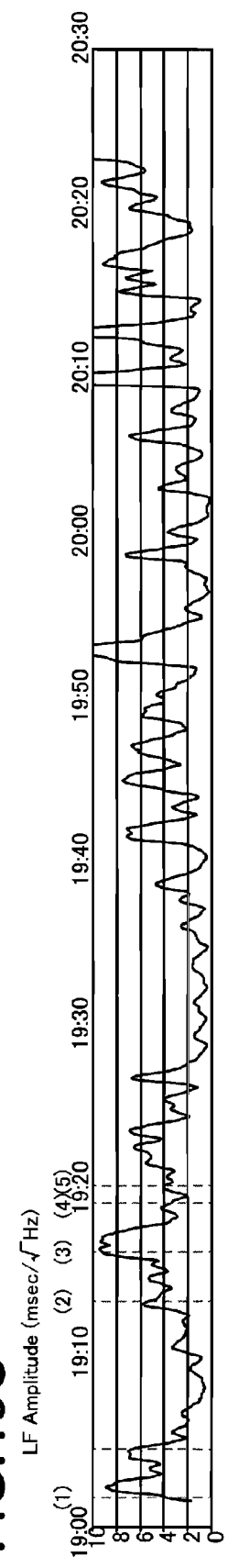
Figure 19D:
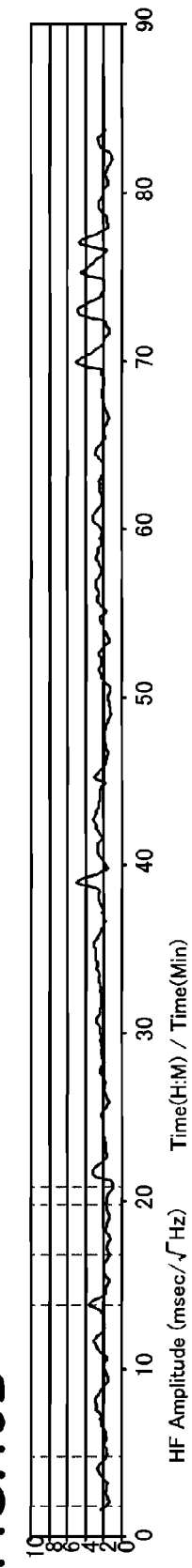

(2) In the above embodiment, although the average values of the R wave peak value LF component and the RR interval HF component over a predetermined time are used as is, a high-frequency cutoff filter may be applied to these values to be used for judgment. For example, the high-frequency cutoff filter adopting 0.03 Hz as the cutoff frequency is applied to the time-series R wave peak value LF component and the RR interval HF component. The value of the RR interval HF component at this time is indicated in high-frequency cutoff HF amplitude of FIG. 9. The value of the R wave peak value LF component at this time is indicated in high-frequency cutoff LF amplitude of FIG. 10. Further, FIG. 11C shows the transition of the R wave peak value LF component (i.e. the average in five seconds) after the high-frequency cutoff filtering. FIG. 12D shows the transition of the RR interval HF component (i.e. the average in five seconds) after the high-cut filtering. By performing high-cut filtering in this way, it is possible to more clearly judge the pain.

(3) Pain may be judged in combination with not only the R wave peak value LF component and the RR interval HF component but also the R wave peak value HF component. That is, when these three components increase, it is judged that there is pain, so that more accurate judgment is possible.

In HF amplitude of FIG. 10, data examples of the R wave peak value HF component are shown. Further, FIG. 11B is the graph showing the temporal transition of the R wave peak value HF component. In the portions of (1), (2), (4), (5), (7), and (8), the increase in the R wave peak value component is observed. Even in this case, it is possible to perform high-frequency cutoff filtering.

FIG. 13 and FIG. 14 show transitions of the R wave peak value LF component, the RR interval HF component, and the R wave peak value HF component when the patient runs without being given pain. FIG. 13A shows the R wave peak value LF component, FIG. 14B shows the RR interval HF component, and FIG. 13B shows the R wave peak value HF component. FIG. 13C, FIG. 14D, and FIG. 13D show the waveform to which high-frequency cutoff filtering is applied on the waveform of FIG. 13A, FIG. 14B and FIG. 13B, respectively.

In this case, sine the R wave peak value HF component does not increase, it can be judged that there is no pain.

(4) Note that the above judgment is made using the R wave peak value LF component and the RR interval HF component (also the R wave peak value HF component). However, another peak value such as a P wave, Q wave, S wave, or T wave, or an ST value may be used instead of the R wave peak value. For example, FIG. 15A shows the LF component of the T wave peak value, and FIG. 15B shows the HF component of the T wave peak value. Similar to the R wave peak value, these components are observed to increase according to the events (1), (2), (4), (5), (7), and (8) relative to pain. FIG. 15C and FIG. 15D show the waveform to which high-frequency cutoff filtering is applied on the waveform of FIG. 15A and FIG. 15B, respectively.

Further, FIG. 16A shows the LF component of the ST value, and FIG. 16B shows the HF component of the ST value. FIG. 16C and FIG. 16D show the waveform to which high-frequency cutoff filtering is applied on the waveform of FIGS. 16A and 16B, respectively. Similar to the R wave peak value, these components are observed to increase according to the events (1), (2), (4), (5), (7), and (8) relative to pain.

(5) In the above embodiment, influence of the noise is eliminated using the RR interval HF component. However, an HF component of the interval between pulses of given characteristic points (for example, point P or point Q) of the electrocardiographic complex may be used. Further, an HF component of the time interval between two given characteristic points within a single pulse may be used. FIG. 17A shows the LF component of a QRS interval within a single pulse, and FIG. 17B shows the HF component of the QRS interval. FIG. 17C, FIG. 17D shows the waveform to which high-frequency cutoff filtering is applied on the waveform of FIGS. 17A and 17B. Similar to the RR interval HF component, immediately after (3) and (6) where no pain is given, the increase in the QRS interval HF component is not observed.

Further, instead of the RR interval HF component or together with this, based on a change in the skin potential or skin resistance or the presence or absence of the myoelectric signal superimposed on an electrocardiographic complex, the influence of noise may be eliminated. For example, when the skin resistance is a predetermined value or more, it is judged that there is no pain even if the R wave peak value LF component increases. When the skin potential (i.e. the difference in potential between two points of the skin, for example, SPL (skin potential level) or SPR (skin potential response)) is smaller than a predetermined value, it is judged that there is no pain even if the R wave peak value Lf component increases. Further, when the myoelectric signal is acquired by applying to the electrocardiographic complex a band-pass filter that passes 10 to 40 Hz and the magnitude of the myoelectric signal exceeds a predetermined value, it may be judged that there is no pain even if the R wave peak value LF component increases.

(6) In the above embodiment, although the average value is used to calculate the LF component and the HF component, the maximum value or area value may be used.

(7) In the above embodiment, the target is people, and therefore, in FIG. 8, the range to calculate the LF component is set to 0.04 Hz to 0.15 Hz and the range to calculate the HF component is set to 0.15 Hz to 0.4 Hz. However, when pain is judged targeting at animals, the range needs to be set as shown in the following table 1.

TABLE 1

| | Frequency Band (Hz) | |
|---|---|---|
| | LF Range | HF Range |
| Humans | 0.04 to 0.15 | 0.15 to 0.4 |
| Large Animals (e.g. Dog) | 0.05 to 0.2 | 0.2 to 2 |
| Middle-sized Animals (e.g. Rabbit)) | 0.04 to 0.28 | 0.28 to 2 |
| Small Animals (e.g. Rat) | 0.27 to 0.74 | 0.74 to 2 |

(8) In each of the above embodiments, although pain judgment is output, the graphs shown in FIG. 11 and FIG. 12 may be output and displayed on the display 28 so as to be judged by people.

(9) Although this invention is configured as the pain judging device in the above embodiment, it may be applied as an electrocardiographic monitor with a pain judging function.

(10) In the above embodiment, the "fluctuation" is quantified by calculating the HF component and the LF component. However, judgment may be made by quantifying the "fluctuation" based on other component, for example, peak value of the HF wave or the LF wave or the degree of steepness of the HF wave or the LF wave.

(11) In the above embodiment, pain is judged by receiving the electrocardiographic complex and extracting the characteristic values of, for example, the R wave peak value and the RR interval. However, pain may also be judged by receiving the extracted characteristic values from outside.

(12) In the above embodiment, the R wave peak value LF component is the primary element to judge pain, and the RR interval HF component and the R wave peak value HF component are secondary judgment elements. However, the RR interval HF component or the R wave peak value HF component may be the primary element, and the other components may be secondary judgment elements.

(13) In the above embodiment, pain is judged based on the fluctuation of the peak-relevant value or the interval value. However, pain may also be directly judged based on the peak-relevant value or the interval value.

(14) In the above embodiment, although each function in FIG. 1 is realized using the computer, part or all of functions may be realized by a hardware logic circuit.

What is claimed is:

1. A pain judging device comprising:
    an electrocardiographic information acquiring unit for acquiring electrocardiographic information measured in a measuring unit;
    pain judging means for judging a degree of pain based on analysis of a frequency of a peak value of a P wave, a Q wave, an R wave, an S wave, a T wave, or an ST of the electrocardiographic information; and
    outputting means for outputting a judgment result by the pain judging means for treatment of a patient,
    wherein the pain judging means comprises:
    peak value frequency analyzing means for analyzing a frequency of the peak value acquired as time-series data;
    peak value Low Frequency (LF) component calculating means for calculating as a peak value LF component an LF component based on a frequency component of a peak value acquired by the peak value frequency analyzing means, and
    wherein the peak value LF component is acquired as characteristics of fluctuation of a peak value.

2. The pain judging device according to claim 1, wherein the pain judging means comprises noise eliminating means for improving accuracy of pain judgment based on the fluctuation related to the peak value.

3. The pain judging device according to claim 2, wherein the noise eliminating means for eliminating influence of the noise using, as an index, fluctuation of an interval between characteristic points of the electrocardiographic complex, myoelectric information, or a skin resistance or a skin potential measured by a second measuring unit.

4. The pain judging device according to claim 1, wherein the pain judging means judges that there is pain when the peak value Low Frequency (LF) component increases.

5. The pain judging device according to claim 1, wherein the pain judging means comprises:
    interval frequency analyzing means for analyzing a frequency of an interval between waveform characteristic points of the electrocardiographic information acquired as time-series data;
    interval High Frequency (HF) component calculating means for calculating as an interval HF component an HF component based on a frequency component of the interval between the waveform characteristic points that are acquired by the interval frequency analyzing means, and
    wherein the interval HF component is acquired as characteristics of fluctuation of an interval.

6. The pain judging device according to claim 5, wherein the interval HF component is an index indicating a respiratory fluctuation component acquired from a frequency component of an interval between waveform characteristic points that are acquired by the interval frequency analyzing means.

7. The pain judging device according to claim 5, further comprising:
    peak value LF component calculating means for calculating as a peak value LF component an LF component based on a frequency component of a peak value acquired by the peak value frequency analyzing means, and
    wherein the pain judging means judges that there is pain when an interval HF component does not decrease and a peak value LF component increases.

8. The pain judging device according to claim 1, wherein the pain judging means comprises:
    peak value frequency analyzing means for analyzing a frequency of the peak value acquired as time-series data;
    peak value High Frequency (HF) component calculating means for calculating as a peak value HF component an HF component based on a frequency component of a peak value that is acquired by the peak value frequency analyzing means, and
    wherein the peak value HF component is acquired as characteristics of fluctuation of a peak value.

9. The pain judging device according to claim 8, further comprising:
    peak value Low Frequency (LF) component calculating means for calculating as a peak value LF component and LF component based on a frequency component of a peak value acquired by the peak value frequency analyzing means, and
    wherein the pain judging means judges that there is pain when an interval HF component does not decrease and a peak value LF component and a peak value HF component both increase.

10. A pain judging device comprising:
    an electrocardiographic information acquiring unit adapted to acquire electrocardiographic information measured in a measuring unit;
    pain judging means for judging a degree of pain based on analysis of a frequency of a peak value of the electrocardiographic information; and
    an outputting unit adapted to output a judgment result by the pain judging means for treatment of a patient,
    wherein the pain judging means comprises:
    peak value frequency analyzing means for analyzing a frequency of the peak value acquired as time-series data;
    peak value Low Frequency (LF) component calculating means for calculating as a peak value LF component an LF component based on a frequency component of a peak value acquired by the peak value frequency analyzing means, and
    wherein the peak value LF component is acquired as characteristics of fluctuation of a peak value.

* * * * *